United States Patent
Goodhew

(10) Patent No.: US 8,377,914 B2
(45) Date of Patent: Feb. 19, 2013

(54) METHOD OF INDUCING NEGATIVE CHEMOTAXIS

(75) Inventor: Erica Brook Goodhew, Atlanta, GA (US)

(73) Assignee: Celtaxsys, Inc., Atlanta, GA (US)

( * ) Notice: Subject to any disclaimer, the term of this patent is extended or adjusted under 35 U.S.C. 154(b) by 334 days.

(21) Appl. No.: 12/576,434

(22) Filed: Oct. 9, 2009

(65) Prior Publication Data

US 2010/0093677 A1 Apr. 15, 2010

Related U.S. Application Data

(60) Provisional application No. 61/104,561, filed on Oct. 10, 2008.

(51) Int. Cl.
*A01N 45/00* (2006.01)
*A01N 43/00* (2006.01)
*A01N 43/54* (2006.01)
*A61K 31/59* (2006.01)
*A61K 31/55* (2006.01)
*A61K 31/505* (2006.01)

(52) U.S. Cl. .................. 514/167; 514/212; 514/269

(58) Field of Classification Search .................. 514/167, 514/212, 269
See application file for complete search history.

(56) References Cited

U.S. PATENT DOCUMENTS

| 2003/0017141 A1 | 1/2003 | Poznansky et al. |
| 2004/0087584 A1 | 5/2004 | Schumacher et al. |
| 2004/0146539 A1 | 7/2004 | Gupta |
| 2006/0122133 A1 | 6/2006 | Weinstein |
| 2008/0213319 A1 | 9/2008 | Kang et al. |

FOREIGN PATENT DOCUMENTS

| WO | 2006/122007 A1 | 11/2006 |
| WO | 2007022537 A2 | 2/2007 |
| WO | 2007041643 A1 | 4/2007 |
| WO | 2007053622 A2 | 5/2007 |

OTHER PUBLICATIONS

Johnson et. al. (American Family Physician (2000) 61:2703-2710).*
Soares, A.C., et al., "Impaired host defense to *Klebsiella pneumoniae* infection in mice treated with the PDE4 inhibitor rolipram," British Journal of Pharmacology, 140(15): 855-862 (2003).
Matsukawa, Y., et al., "Prevalence of Helicobacter pylori in NSAID users with gastric ulcer," Rheumatology, 42(8): 947-950 (2003).
Flisiak, R., et al., "Effect of lamivudine treatment on plasma levels of transforming growth factor B1, tissue inhibitor of metalloproteinases-1 and metalloproteinase-1 in patients with chronic hepatitis B," World J. Gastroenterol, 10(18): 2661-2665 (2004).
Vonend, O., et al., "Modulation of gene expression by moxonidine in rats with chronic renal failure," Nephrol Dial Transplant, 19(9): 2217-2222 (2004).
Vianello, F., et al., "Fugetaxis: active movement of leukocytes away from a chemokinetic agent," Journal of Molecular Medicine, 83(10): 752-763 (2005).
ZS-Nagy, et al., "Chemistry, toxicology, pharmacology and pharmacokinetics of idebenone: a review," Archives of Gerontology and Geriatrics, 11: 177-186 (1990).

* cited by examiner

*Primary Examiner* — Marcos Sznaidman
(74) *Attorney, Agent, or Firm* — Elmore Patent Law Group, PC; Mahreen Chaudhry Hoda, Esq.; Carolyn S. Elmore, Esq.

(57) ABSTRACT

The current invention is directed to methods of inducing the negative chemotaxis of a migratory cell comprising contacting the cell with a compound selected from the group consisting of idebenone, benazepril, rolipram, moxonidine, lamivudine, loxoprofen, terbinafine, Synephrine, 6-aminoindazole, and a Vitamin D analog, or a pharmaceutically acceptable salt of any of thereof.

4 Claims, 28 Drawing Sheets

METHOD OF INDUCING NEGATIVE CHEMOTAXIS

RELATED APPLICATION

This application claims the benefit of U.S. Provisional Application No. 61/104,561, filed Oct. 10, 2008. The entire teachings of the above application are incorporated herein by reference.

BACKGROUND OF THE INVENTION

Chemotaxis, or the oriented movement of a cell in response to a chemical agent, is a complex and highly integrated process. The movement can be positive (toward) or negative (away) from a chemical gradient. Movement toward an agent or stimulus is termed positive chemotaxis (i.e., the agent or stimulus is chemoattractive for the cell), while movement away from an agent or stimulus is termed negative chemotaxis (i.e., the agent or stimulus is chemorepulsive for the cell). It is believed that for both prokaryotes and eukaryotes, cells undergoing chemotaxis sense a change in agent concentration and, thereby, move in response to the concentration gradient. Chemoattraction (CA) and chemorepulsion (CR) are therefore properties of the agent or stimulus, while chemotaxis is a property of cells.

Within the immune system, chemotaxis is often driven by a class of biological agents, known as chemokines (or chemotactic cytokines). Once triggered, chemotaxis plays an important role in various physiologic and cellular processes including tissue organization, organogenesis homeostasis, embryonic morphogenesis tissue repair and regeneration and disease progression in cancer, mental retardation, atherosclerosis, and arthritis. Compounds that affect chemotaxis (either induce positive or negative chemotaxis) would therefore be useful in modulating these and other biologic processes. Compounds that induce negative chemotaxis have in fact been described as useful in treating inflammation, in inhibiting tumor metastasis and in contraception.

It would therefore be advantageous to identify additional compounds that induce negative chemotaxis.

SUMMARY OF THE INVENTION

The present invention provides methods of inducing the negative chemotaxis of a migratory cell comprising contacting the cell with a compound selected from the group selected from the group consisting of idebenone, benazepril, rolipram, moxonidine, lamivudine, loxoprofen, terbinafine, synephrine, 6-aminoindazole, and a Vitamin D analog, or pharmaceutically acceptable salts thereof.

In another embodiment, the invention is a method of inducing negative chemotaxis of a human immune cell comprising administering a compound selected from the group consisting of idebenone, benazepril, rolipram, moxonidine, lamivudine, loxoprofen, terbinafine, synephrine, 6-aminoindazole and a Vitamin D analog, or pharmaceutically acceptable salts thereof.

In yet another embodiment, the invention is a method of treating a condition mediated by migration of a human migratory cell toward a chemotactic site comprising administering to said patient a compound selected from the group consisting of idebenone, benazepril, rolipram, moxonidine, lamivudine, loxoprofen, terbinafine, synephrine, 6-aminoindazole, and a Vitamin D analog, or pharmaceutically acceptable salts thereof, wherein the compound is administered in an amount effective to inhibit migration of the cell toward the chemotactic site.

In a further embodiment, the invention is a method of treating a patient suffering from an inflammatory condition comprising administering to said patient a compound selected from the group consisting of idebenone, benazepril, rolipram, moxonidine, lamivudine, loxoprofen, terbinafine, synephrine, 6-aminoindazole, and a Vitamin D analog, or pharmaceutically acceptable salts thereof, wherein the compound is administered in a therapeutically effective amount.

In an additional embodiment, the invention is a method of inhibiting angiogenesis comprising administering to said patient a compound selected from the group consisting of idebenone, benazepril, rolipram, moxonidine, lamivudine, loxoprofen, terbinafine, synephrine, 6-aminoindazole, and a Vitamin D analog, or pharmaceutically acceptable salts thereof, wherein the compound is administered in a therapeutically effective amount.

In yet another embodiment, the invention is a method of contraception comprising in a patient in need thereof comprising administering a compound selected from the group consisting of idebenone, benazepril, rolipram, moxonidine, lamivudine, loxoprofen, terbinafine, synephrine, 6-aminoindazole, and a Vitamin D analog, or pharmaceutically acceptable salts thereof in an amount effective to inhibit migration of germ cells in the subject.

In some embodiments, the compound is a Vitamin D analog. In other embodiments, the Vitamin D analog is selected from the group consisting of calcitriol, calcipotriene, ergocalciferol and cholecalciferol. In a further embodiment, the Vitamin D analog is calcitriol.

These and other aspects of the invention, as well as various advantages and utilities, will be more apparent with reference to the drawings and the detailed description of the embodiments of the invention.

DETAILED DESCRIPTION OF THE INVENTION

Figure 1A:
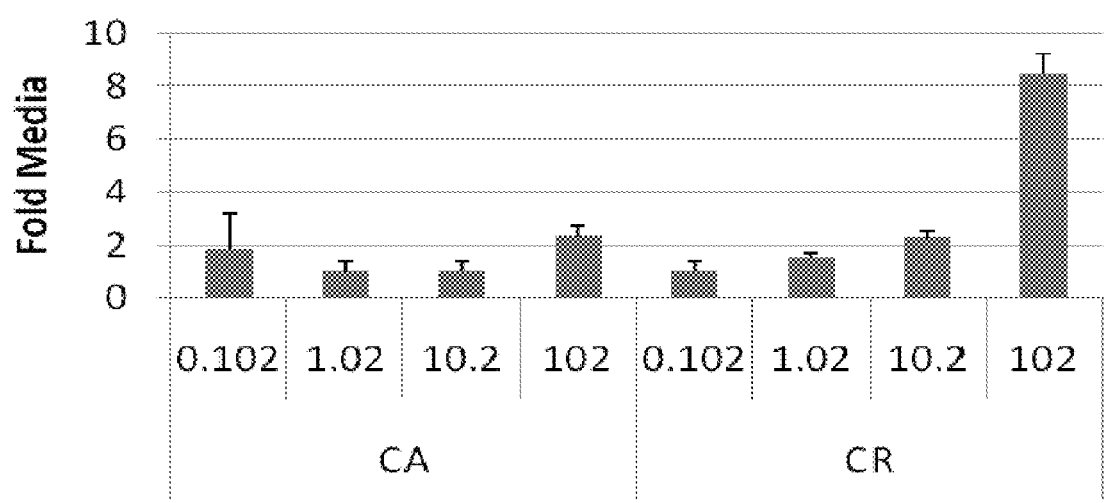
FIG. 1A is a bar graph showing fold induction (over media) of chemorepulsion (right) and chemoattraction (left) of neutrophils treated with 0.102, 1.02, 10.2 and 102 uM idebenone.

A description of the embodiments of the invention follows.

As used herein, "a" or "an" are taken to mean one or more unless otherwise specified.

The present invention is based on the surprising discovery that the compounds idebenone, benazepril, rolipram, moxonidine, lamivudine, calcitriol, calcipotriene, ergocalciferol, cholecalciferol, loxoprofen, terbinafine, Synephrine and 6-aminoindazole and pharmaceutically acceptable salts thereof induce negative chemotaxis of human migratory cell. For example, as shown in Example 1, neutrophils contacted with 102 uM idebenone showed between about 3 and 8-fold greater induction of chemotaxis than that in response to media.

Idebenone (6-(10-hydroxydecyl)-2,3-dimethoxy-5-methyl-1,4-benzoquinone) is a synthetic analog of the antioxidant Coenzyme Q10. Idebenone has been described as promoting nerve growth factor (NGF) in the brain (Nitta et al. 1993. Neurosci Lett. 163(2):219-22). Idebenone has been described as useful for the treatment of Alzheimer's disease (Senin et al., (1992). Arch Gerontol Geriatr. 1992 November-December; 15(3):249-60; U.S. Pat. No. 5,059,627) and Friedrich's ataxia (Tonon et al. (2008). Expert Opin Pharmacother. 2008 September; 9(13):2327-37). Idebenone has the chemical structure shown below:

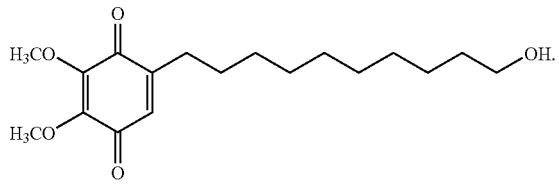 [SMILES: COC1=C(OC)C(=O)C(CCCCCCCCCCO)=CC1=O]

Benazepril is an angiotensin-converting enzyme (ACE) inhibitor and is marketed under the trade name LOTENSIN® for the treatment hypertension (Gomez et al. (1991). Clin Cardiol. 1991 August; 14(8 Suppl 4):IV22-7. Kuhn et al. AACN Clin Issues Crit. Care Nurs. 1992 May; 3(2):461-71). Benazepril has also been described as useful in the treatment of congestive heart failure (Kuhn et al.) and chronic renal insufficiency (Maschio et al. (1996). N Engl J. Med. 1996 Apr. 11; 334(15):939-45). Benazepril has the following chemical structure:

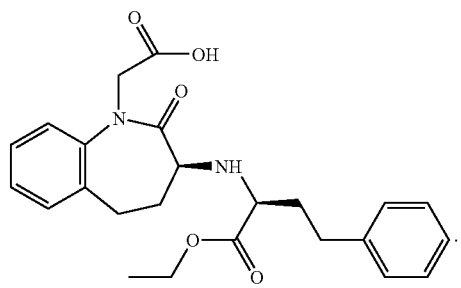 [SMILES: CCOC(=O)[C@H](CCc1ccccc1)N[C@H]1CCc2ccccc2N(CC(=O)O)C1=O]

Rolipram (4-(3-cyclopentyloxy-4-methoxy-phenyl)pyrrolidin-2-one) is a phosphodiesterase-4 (PDE-4) inhibitor and has been shown to inhibit the production of tumor necrosis factor (TNF) alpha (Prabhakar et al. (1994). Int J. Immunopharmacol. 1994 October; 16(10):805-16). Rolipram has been described as useful as an anti-inflammatory agent (Dyke (2002) Expert Opin Investig Drugs. 11(1):1-13) and as an antidepressant (Zhu et al. (2001). CNS Drug Rev. Winter; 7(4):387-98). Rolipram has the chemical structure shown below:

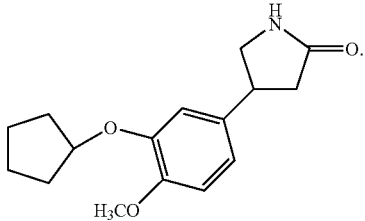 [SMILES: COc1ccc(C2CNC(=O)C2)cc1OC1CCCC1]

Moxonidine is a centrally acting anti-hypertensive agent (Chrisp et al. (1992). Drugs. 44(6):993-1012) and acts as a selective agonist of the imidazoline receptor subtype 1 (Ernsberger et al. (1994). Cardiovasc Drugs Ther. Suppl 1:27-41). Moxonidine has the following chemical structure:

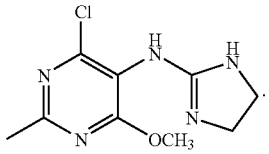 [SMILES: COc1nc(C)nc(Cl)c1NC1=NCCN1]

Lamivudine (4-amino-1-[(2R,5S)-2-(hydroxymethyl)-1, 3-oxathiolan-5-yl]pyrimidin-2-one) is a nucleoside analog reverse transcriptase inhibitor. Lamivudine has been used in the treatment of hepatitis B (Rousssos et al. (2008). Acta Gastroenterol Belg. 71(1):30-2) and HIV (Perry et al. (1997), 53(4):657-80). Lamivudine is marketed under the trade names ZEFFIX® and EPIVIR® and has the chemical structure shown below:

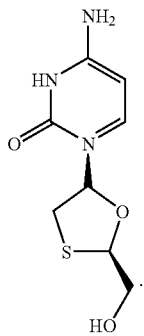

Loxoprofen is a non-steroidal anti-inflammatory drug that inhibits cyclooxygenase (Noguchi et al. (2005) Biol Pharm Bull 28(11): 2075-79). Loxoprofen sodium has the chemical structure shown below:

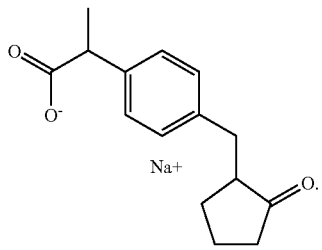 [SMILES: CC(C(=O)[O-])c1ccc(CC2CCCC2=O)cc1 ; [Na+]]

Terbinafine (N,6,6-trimethyl-N-(naphthalen-1-ylmethyl) hept-2-en-4-yn-1-amine) is a synthetic allylamine antifungal agent that inhibits ergosterol synthesis (Leyden (1998). J Am Acad Dermatol. 1998 May; 38(5 Pt 3):S42-7). Terbinafine hydrochloride is marketed under the trade names LAMISIL® and TERBISIL® for the treatment of onychomycosis and other fungal infections (Balfour et al. (2002) Drugs. 1992 February; 43(2):259-84). Terbinafine has the chemical structure shown below:

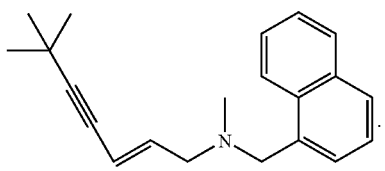 [SMILES: CN(C/C=C/C#CC(C)(C)C)Cc1cccc2ccccc12]

Synephrine is derived from *Citrus aurantium* and has been described as having lipolytic effects on human fat cells (Fugh-Berman et al. (2004). Exp Biol Med (Maywood). 229 (8):698-704. Synephrine has the following chemical structure:

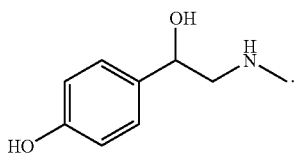

6-aminoindazole has been shown to suppress gastric acid secretion (Pinelli et al. (1989). Arzneimittelforschung. 1989 March; 39(3):361-5). 6-aminoindazole has the chemical structure shown below:

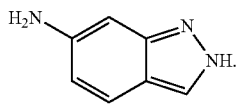

Vitamin D is a group prohormones with several active metabolites that act as hormones. Vitamin D includes cholecalciferol (Vitamin D3) and ergocalciferol (Vitamin D2). 7-dehydroxycholesterol is found in the skin and when exposed to sunlight is converted to cholecalciferol. Ergosterol, found in plants, is the provitamin for Vitamin D2 (ergocalciferol). The primary active metabolite of Vitamin D is calcitriol (1,25-dihydroxyvitamin D). The term "Vitamin D analog" encompasses Vitamin D, Vitamin D metabolites and synthetic derivatives thereof (Goodman and Gilman, The Pharmacologic Basis of Therapeutics). Synthetic derivatives of Vitamin D include, for example, dihydrotachysterol, 25-hydroxydihydrotachysterol, 1α-hydroxycholecalciferol, calcipotriol and 22-oxacalcitriol. Vitamin D analogs include, but are not limited to, cholecalciferol, ergosterol, calcitriol, 25(OH)D3, dihydrotachysterol, 25-hydroxydihydrotachysterol, 1α-hydroxycholecalciferol, 25-hydroxycholecalciferol, calcipotriol, 22-oxacalcitriol, ergocalciferol, 1α-25-dihydroxyergocalciferol, 22,23-dihydroergocalciferol, 1,24,25-trihydroxycholecalciferol, previtamin D3, tacalciol, isovitamin D3, dihydrotachysterol3, (1S)-hydroxycalciol, (24R)-hydroxycalcidiol, 25-fluorocalciol, ercalcidiol, ertacalciol, (5E)-isocalciol, 22,23-dihydroercalciol, (24S)-methylcalciol, (5E)-(10S)-10,19-dihydroercalciol, (24S)-ethylcalciol, 22-dihydroergocalciferol, calcifidiol and (22E)-(24R)-ethyl-22,23-didehydrocalciol. Other Vitamin D analogs, have been described, for example in U.S. Pat. No. 4,851,401 (cyclopentano-vitamin D analogs), U.S. Pat. No. 5,120,722 (trihydroxycalciferol derivatives), U.S. Pat. No. 5,446,035 (20-methyl substituted vitamin D), U.S. Pat. No. 5,411,949 (23-oxa-derivatives), U.S. Pat. No. 5,237,110 (19-nor-vitamin D compounds), U.S. Pat. No. 4,857,518 (hydroxylated 24-homo-vitamin D derivatives). Other Vitamin D analogs are taught in U.S. Pat. Nos. 4,804,502; 4,866,048; 5,145,846 5,374,629; 5,403,940; 5,446,034; and 5,447,924, 7,115,758, 7,312,249, 7,241,752, 7,361,664. Calcitriol analogs include, but are not limited to, calcipotriene, Vitamin D2, Vitamin D3, 1α-OH-Vitamin D3, 1α-OH-Vitamin D2, calcifediol, Vitamin D4, 1α-25-dihydroxyvitamin D3, 19-nor-1,25-dihydroxyvitamin D2, 24-homo-22-dehydro-22E-1α-25-dihydroxyvitamin D3, 1,25-dihydroxy-24(E)-dehydro-24-homo-vitamin D$_3$, and 19-nor-1,25-dihydroxy-21-epi-vitamin D3.

Calcitriol increases absorption of calcium and phosphate in the gastrointestinal tract (Favus et al. (1985). Am J. Physiol., 248(2 Pt 1):G147-57). Calcitriol is marketed as ROCALTROL®, CALCIJEX® and DECOSOTRIOL® and has the following chemical structure:

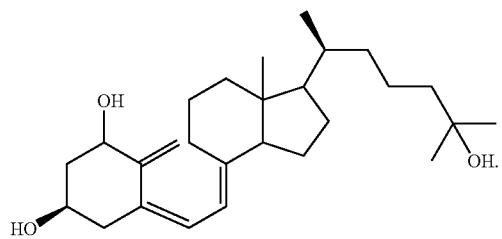 [SMILES: C=C1/C(=C\C=C2/CCCC3(C)C2CCC3[C@@H](C)CCCC(C)(C)O)C[C@@H](O)CC1O]

The term "chemorepellant Vitamin D analog" refers to a Vitamin D analog that is capable of inducing negative chemotaxis of a human migratory cell. In certain aspects, the chemorepellant Vitamin D analog is selected from the group consisting of calcitriol, calcipotriene, ergocalciferol and cholecalciferol.

Pharmaceutically acceptable salts of the compounds described above are non-toxic, inorganic and organic acid and base addition salts. Exemplary acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, trifluoro acetic acid and the like. Sample base-addition salts include those derived from ammonium, potassium, sodium and, quaternary ammonium hydroxides, such as, for example, tetramethylammonium hydroxide. Chemical modification of a pharmaceutical compound (i.e. drug) into a salt is a technique well known to pharmaceutical chemists to obtain improved physical and chemical stability, hygroscopicity, flowability and solubility of compounds. See, e.g., Ansel et al., Pharmaceutical Dosage Forms and Drug Delivery Systems (6th Ed. 1995) at pp. 196 and 1456-1457.

As used herein, "migratory cells" are those cells which are capable of movement from one place to another in response to a stimulus. Human migratory cells include those involved in the processes of cancer, immunity, angiogenesis or inflammation and also include those identified to play a role in other disease states or conditions. Migratory cells include, but are not limited to, immune cells, hematopoietic cells, neural cells, epithelial cells, mesenchymal cells, stem cells, germ cells and cells involved in angiogenesis.

Immune cells include, but are not limited to, monocytes, Natural Killer (NK) cells, dendritic cells (which could be immature or mature), subsets of dendritic cells including myeloid, plasmacytoid (also called lymphoid) or Langerhans; macrophages such as histiocytes, Kupffer's cells, alveolar macrophages or peritoneal macrophages; neutrophils, eosinphils, mast cells, basophils; B cells including plasma B cells, memory B cells, B-1 cells, B-2 cells; CD45RO (naive T), CD45RA (memory T); CD4 Helper T Cells including Th1, Th2 and Tr1/Th3; CD8 Cytotoxic T Cells, Regulatory T Cells and Gamma Delta T Cells.

Hematopoietic cells include, but are not limited to, pluripotent stem cells, multipotent progenitor cells and/or progenitor cells committed to specific hematopoietic lineages. The progenitor cells committed to specific hematopoietic lineages can be of T cell lineage, B cell lineage, dendritic cell lineage, neutrophil lineage, Langerhans cell lineage and/or lymphoid tissue-specific macrophage cell lineage. The hematopoietic cells can be derived from a tissue such as bone marrow, peripheral blood (including mobilized peripheral blood), umbilical cord blood, placental blood, fetal liver, embryonic cells (including embryonic stem cells), aortal-gonadal-mesonephros derived cells, and lymphoid soft tissue. Lymphoid soft tissue includes the thymus, spleen, liver, lymph node, skin, tonsil and Peyer's patches. In other embodiments, hematopoietic cells can be derived from in vitro cultures of any of the foregoing cells, and in particular in vitro cultures of progenitor cells.

Neural cells are cells of neural origin and include neurons and glia and/or cells of both central and peripheral nervous tissue.

Epithelial cells include cells of a tissue that covers and lines the free surfaces of the body. Such epithelial tissue includes cells of the skin and sensory organs, as well as the specialized cells lining the blood vessels, gastrointestinal tract, air passages, lungs, ducts of the kidneys and endocrine organs.

Mesenchymal cells include, but are not limited to, cells that express typical fibroblast markers such as collagen, vimentin and fibronectin.

Cells involved in angiogenesis are cells that are involved in blood vessel formation and include cells of endothelial origin and cells of mesenchymal origin.

Germ cells are cells specialized to produce haploid gametes.

In certain embodiment, the human migratory cell is an immune cell. In other embodiments, the immune cell is selected from the group consisting of lymphocytes, monocytes, neutrophils, eosinophils and mast cells. In a further embodiment, the immune cell is a neutrophil or an eosinophil.

As used herein, the terms "contact" or "contacting" means the act of touching or bringing together two entities or things in such proximity as will allow an influence of at least one on the other. The definition, while inclusive of physical contact is not so limited.

As used herein, a "chemorepellant" is an agent or stimulus that induces, elicits or triggers negative chemotaxis of a migratory cell. A "chemoattractant" is an agent or stimulus that induces, elicits or triggers positive chemotaxis (movement towards an agent or stimulus) by a migratory cell. Compounds selected from the group consisting of idebenone, benazepril, rolipram, moxonidine, lamivudine, calcitriol, loxoprofen, terbinafine, Synephrine and 6-aminoindazole or pharmaceutically acceptable salts thereof have been discovered to be chemorepellants. As used herein the terms "induce," "elicit," and "trigger," when referring to the activity of a chemorepellant or chemoattractant with respect to negative or positive chemotaxis, carry the same meaning The term "agent" refers generally to any chemical compound or biologic.

Based on their ability to induce negative chemotaxis, compounds selected from the group consisting of idebenone, benazepril, rolipram, moxonidine, lamivudine, loxoprofen, terbinafine, synephrine, 6-aminoindazole and Vitamin D analogs, or pharmaceutically acceptable salts thereof are useful inhibiting the induction of chemotaxis of migratory cells toward a chemotactic site. As used herein, a "chemotactic site" is a site that induces positive chemotaxis of migratory cells. Chemotactic sites include sites of inflammation, medical implants, transplants and angiogenesis.

Compounds selected from the group consisting of idebenone, benazepril, rolipram, moxonidine, lamivudine, loxoprofen, terbinafine, synephrine, 6-aminoindazole, Vitamin D analogs, or pharmaceutically acceptable salts thereof are useful for inhibiting the induction of chemotaxis of migratory cells toward a site of inflammation. Inhibiting migratory cell chemotaxis toward a site of inflammation can result in a reduction or amelioration of an inflammatory response in situations such as bacterial infection, tissue injury-induced inflammation (e.g., ischemia-reperfusion injury), complement-induced inflammation, oxidative stress (e.g., hemodialysis), immune complex-induced inflammation (e.g., antibody-mediated glomerunephritis), cytokine-induced inflammation (e.g., rheumatoid arthritis), antineutrophil cytoplasmic antibodies and vasculitis (e.g., autoimmunity against neutrophil components), genetic disorders of neutrophil regulations (e.g., hereditary periodic fever syndromes), implant related inflammation, and cystic fibrosis.

In certain embodiments, the invention is a method of treating an inflammatory condition in a patient suffering therefrom comprising administering to said patient a compound selected from the group consisting of idebenone, benazepril, rolipram, moxonidine, lamivudine, loxoprofen, terbinafine, synephrine, 6-aminoindazole, Vitamin D analogs, or pharmaceutically acceptable salts thereof in a therapeutically effective amount. Inflammatory conditions include, but are not limited to, appendicitis, peptic, gastric or duodenal ulcers, peritonitis, pancreatitis, acute or ischemic colitis, diverticulitis, epiglottitis, achalasia, cholangitis, cholecystitis, hepatitis, inflammatory bowel disease (including, for example, Crohn's disease and ulcerative colitis), enteritis, Whipple's disease, asthma, chronic obstructive pulmonary disease, acute lung injury, ileus (including, for example, post-operative ileus), allergy, anaphylactic shock, immune complex disease, organ ischemia, reperfusion injury, organ necrosis, hay fever, sepsis, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, cystic fibrosis, pneumonitis, pneumoultramicroscopic silicovolcanoconiosis, alvealitis, bronchiolitis, pharyngitis, pleurisy, sinusitis, influenza, respiratory syncytial virus, herpes, disseminated bacteremia, Dengue fever, candidiasis, malaria, filariasis, amebiasis, hydatid cysts, burns, dermatitis, dermatomyositis, urticaria, acne, vasulitis, angiitis, endocarditis, arteritis, atherosclerosis, thrombophlebitis, pericarditis, myocarditis, myocardial ischemia, periarteritis nodosa, rheumatic fever, Alzheimer's disease, celiac disease, congestive heart failure, adult respiratory distress syndrome, meningitis, encephalitis, multiple sclerosis, cerebral infarction, cerebral embolism, Guillame-Barre syndrome, neuritis, neuralgia, uveitis, arthritides, arthralgias, osteomyelitis, fasciitis, Paget's disease, gout, periodontal disease, rheumatoid arthritis, synovitis, myasthenia gravis, thryoiditis, systemic lupus erythematosus, Goodpasture's syndrome, Behcet's syndrome, allograft rejection, graft-versus-host disease, Type I diabetes, ankylosing spondylitis, Berger's disease, Type II diabetes, Retier's syndrome, Hodgkins disease and injection site reaction.

Injection site reaction is a term generally used to describe inflammation in and around a site of injection. Injection site reaction has been observed with the injection of numerous pharmaceutical agents including, but not limited, chemotherapeutic drugs, immunomodulator drugs, and vaccines. The present invention encompasses a method for the treatment or reduction of injection site reaction comprising administration of a compound selected from the group consisting of idebenone, benazepril, rolipram, moxonidine, lamivudine, loxoprofen, terbinafine, synephrine, 6-aminoindazole, Vitamin D analogs, or pharmaceutically acceptable salts thereof. A compound selected from the group consisting of idebenone, benazepril, rolipram, moxonidine, lamivudine, loxoprofen, terbinafine, synephrine, 6-aminoindazole, Vitamin D analogs, or pharmaceutically acceptable salts thereof can, for example, be administered before, during or after injection. In some embodiments, the compound selected from the group consisting of idebenone, benazepril, rolipram, moxonidine, lamivudine, loxoprofen, terbinafine, synephrine, 6-aminoindazole, Vitamin D analogs, or pharmaceutically acceptable salts thereof can be administered topically at the site of the injection.

In another embodiment, the invention is a method of inhibiting positive chemotaxis toward a medical implant. The medical implant can be contacted or coated with a compound selected from idebenone, benazepril, rolipram, moxonidine, lamivudine, loxoprofen, terbinafine, synephrine, 6-aminoindazole, Vitamin D analogs, or pharmaceutically acceptable salts thereof in amount sufficient to induce negative chemotaxis of an immune cell. The compounds can also be administered locally at the site of the medical implant. A medical implant is defined as a device or entity implanted into a surgically or naturally formed cavity of the body. Medical implants include, but are not limited to, stents, pacemakers, pacemaker leads, defibrillators, drug delivery devices, sensors, pumps, embolization coils, sutures, electrodes, cardiovascular implants, arterial stents, heart valves, orthopedic implants, dental implants, bone screws, plates, catheters, cannulas, plugs, fillers, constrictors, sheets, bone anchors, plates, rods, seeds, tubes, or portions thereof. In addition to the compound selected from the group consisting of idebenone, benazepril, rolipram, moxonidine, lamivudine, loxoprofen, terbinafine, synephrine, 6-aminoindazole, and Vitamin D analogs, or pharmaceutically acceptable salts thereof, the medical implant can be coated with a cell-growth potentiating agent, an anti-infective agent and/or an anti-inflammatory agent.

In yet another embodiment, the invention is a method of inhibiting positive chemotaxis toward an organ transplant or tissue graft. Organ transplants and tissue grants include, but are not limited to, renal, pancreatic, hepatic, lymphoid and cardiac grafts and organs. Lymphoid grafts include a splenic graft, a lymph node derived graft, a Peyer's patch derived graft, a thymic graft and a bone marrow derived graft. In an additional embodiment, the invention is a method of treating a patient suffering from transplant or graft rejection comprising administering a compound selected from idebenone, benazepril, rolipram, moxonidine, lamivudine, loxoprofen, terbinafine, synephrine, 6-aminoindazole, and a Vitamin D analog, or pharmaceutically acceptable salts thereof.

As discussed above, the compounds described above can be used to inhibit chemotaxis toward a site of angiogenesis. A site of angiogenesis is a site where blood vessels are being formed. In one embodiment, the invention is a method of inducing negative chemotaxis of endothelial cells toward a site of angiogenesis. The invention also encompasses a method of inhibiting angiogenesis in a patient in need thereof comprising administering a compound selected from the group consisting of idebenone, benazepril, rolipram, moxonidine, lamivudine, loxoprofen, terbinafine, synephrine, 6-aminoindazole and a Vitamin D analog, or pharmaceutically acceptable salts thereof in a therapeutically effective amount. In a further embodiment, the invention is a method of treating cancer or a tumor comprising administering a compound selected from idebenone, benazepril, rolipram, moxonidine, lamivudine, loxoprofen, terbinafine, synephrine, 6-aminoindazole, and a Vitamin D analog, or pharmaceutically acceptable salts thereof in an amount effective to inhibit angiogenesis. According to another aspect of the invention, a method of inhibiting endothelial cell migration to a tumor site in a subject is provided. The method involves locally administering to or contacting an area surrounding a tumor site in need of such treatment a compound selected from the group consisting of idebenone, benazepril, rolipram, moxonidine, lamivudine, loxoprofen, terbinafine, synephrine, 6-aminoindazole and a Vitamin D analog, or pharmaceutically acceptable salts thereof in an amount effective to inhibit endothelial cell migration into the tumor site in the subject.

Exemplary cancers and tumors that can be treated according to the methods of the invention include, for example, biliary tract cancer; brain cancer including glioblastomas and medulloblastomas; breast cancer; cervical cancer; choriocarcinoma; colon cancer; endometrial cancer; esophageal cancer, gastric cancer; hematological neoplasms, including acute lymphocytic and myelogenous leukemia; multiple myeloma; AIDS associated leukemias and adult T-cell leukemia lymphoma; intraepithelial neoplasms, including Bowen's disease and Paget's disease; liver cancer (hepatocarcinoma); lung cancer; lymphomas, including Hodgkin's disease and lymphocytic lymphomas; neuroblastomas; oral cancer, including squamous cell carcinoma; ovarian cancer, including those arising from epithelial cells, stromal cells, germ cells and mesenchymal cells; pancreas cancer; prostate cancer; rectal cancer; sarcomas, including leiomyosarcoma, rhabdomyosarcoma, liposarcoma, fibrosarcoma and osteosarcoma; skin cancer, including melanoma, Kaposi's sarcoma, basocellular cancer and squamous cell cancer; testicular cancer, including germinal tumors (seminoma, non-seminoma [teratomas, choriocarcinomas]), stromal tumors and germ cell tumors; thyroid cancer, including thyroid adenocarcinoma and medullar carcinoma; and renal cancer including adenocarcinoma and Wilms tumor.

The invention also encompasses a method of contraception in a patient in need thereof comprising administering a compound selected from idebenone, benazepril, rolipram, moxonidine, lamivudine, loxoprofen, terbinafine, synephrine, 6-aminoindazole and a Vitamin D analog, or pharmaceutically acceptable salts thereof in an amount effective to inhibit migration of germ cells in the subject. According to another aspect of the invention, a method of treating infertility and premature labor is provided. The method comprises administering a compound described above in an amount effective to inhibit immune cells from migrating close to a germ cell in the subject.

The treatment methods disclosed herein involve administering, either locally or systemically, to a selected site in a subject in need of such a treatment the compound selected from idebenone, benazepril, rolipram, moxonidine, lamivudine, loxoprofen, terbinafine, synephrine, 6-aminoindazole and a Vitamin D analog, or pharmaceutically acceptable salts thereof in an amount effective to induce negative chemotaxis of a human migratory cell. As used herein, a "therapeutically effective amount" is an amount sufficient to induce negative migration of a migratory cell and/or ameliorate a disease or condition of a patient or achieve a desired outcome. For example, a "therapeutically effective amount" in reference to the treatment of an inflammatory condition encompasses an amount sufficient to induce negative chemotaxis of an immune cell and/or ameliorate a symptom of the inflammatory condition.

In certain embodiments, the compound selected from idebenone, benazepril, rolipram, moxonidine, lamivudine, loxoprofen, terbinafine, synephrine, 6-aminoindazole, and a Vitamin D analog, or pharmaceutically acceptable salts thereof can be co-administered with a second agent (e.g., another chemoattractant or with any drug or agent which is not itself a chemoattractant). Co-administered agents, compounds, chemoattractants or therapeutics need not be administered at exactly the same time. In certain embodiments, however, the compound selected from idebenone, benazepril, rolipram, moxonidine, lamivudine, loxoprofen, terbinafine, synephrine, 6-aminoindazole and a Vitamin D analog, or pharmaceutically acceptable salts thereof is administered substantially simultaneously as the second agent. By "substantially simultaneously," it is meant that the compound selected from idebenone, benazepril, rolipram, moxonidine, lamivudine, loxoprofen, terbinafine, synephrine, 6-aminoindazole and a Vitamin D analog, or pharmaceutically acceptable salts thereof is administered before, at the same time, and/or after the administration of the second agent. Second agents include, for example, anti-inflammatory agents, anti-cancer agents, anti-infective agents, immune therapeutics (immunosuppresants) and other therapeutic compounds. A second agent can be chosen based on the condition or disease to be treated. For example, in a method of treating cancer or a tumor, the compound selected from idebenone, benazepril, rolipram, moxonidine, lamivudine, loxoprofen, terbinafine, synephrine, 6-aminoindazole, and a Vitamin D analog, or pharmaceutically acceptable salts thereof can be administered with an anti-cancer agent. Similarly, in a method of treating an inflammatory condition, the compound selected from idebenone, benazepril, rolipram, moxonidine, lamivudine, loxoprofen, terbinafine, synephrine, 6-aminoindazole and a Vitamin D analog, or pharmaceutically acceptable salts thereof can be administered with an anti-inflammatory agent, an anti-infective agent or an immunosuppressant.

An anti-infective agent is an agent which reduces the activity of or kills a microorganism and includes: Aztreonam; Chlorhexidine Gluconate; Imidurea; Lycetamine; Nibroxane; Pirazmonam Sodium; Propionic Acid; Pyrithione Sodium; Sanguinarium Chloride; Tigemonam Dicholine; Acedapsone; Acetosulfone Sodium; Alamecin; Alexidine; Amdinocillin; Amdinocillin Pivoxil; Amicycline; Amifloxacin; Amifloxacin Mesylate; Amikacin; Amikacin Sulfate; Aminosalicylic acid; Aminosalicylate sodium; Amoxicillin; Amphomycin; Ampicillin; Ampicillin Sodium; Apalcillin Sodium; Apramycin; Aspartocin; Astromicin Sulfate; Avilamycin; Avoparcin; Azithromycin; Azlocillin; Azlocillin Sodium; Bacampicillin Hydrochloride; Bacitracin; Bacitracin Methylene Disalicylate; Bacitracin Zinc; Bambermycins; Benzoylpas Calcium; Berythromycin; Betamicin Sulfate; Biapenem; Biniramycin; Biphenamine Hydrochloride; Bispyrithione Magsulfex; Butikacin; Butirosin Sulfate; Capreomycin Sulfate; Carbadox; Carbenicillin Disodium; Carbenicillin Indanyl Sodium; Carbenicillin Phenyl Sodium; Carbenicillin Potassium; Carumonam Sodium; Cefaclor; Cefadroxil; Cefamandole; Cefamandole Nafate; Cefamandole Sodium; Cefaparole; Cefatrizine; Cefazaflur Sodium; Cefazolin; Cefazolin Sodium; Cefbuperazone; Cefdinir; Cefepime; Cefepime Hydrochloride; Cefetecol; Cefixime; Cefinenoxime Hydrochloride; Cefmetazole; Cefinetazole Sodium; Cefonicid Monosodium; Cefonicid Sodium; Cefoperazone Sodium; Ceforanide; Cefotaxime Sodium; Cefotetan; Cefotetan Disodium; Cefotiam Hydrochloride; Cefoxitin; Cefoxitin Sodium; Cefpimizole; Cefpimizole Sodium; Cefpiramide; Cefpiramide Sodium; Cefpirome Sulfate; Cefpodoxime Proxetil; Cefprozil; Cefroxadine; Cefsulodin Sodium; Ceftazidime; Ceftibuten; Ceftizoxime Sodium; Ceftriaxone Sodium; Cefuroxime; Cefuroxime Axetil; Cefuroxime Pivoxetil; Cefuroxime Sodium; Cephacetrile Sodium; Cephalexin; Cephalexin Hydrochloride, Cephaloglycin; Cephaloridine; Cephalothin Sodium; Cephapirin Sodium; Cephradine; Cetocycline Hydrochloride; Cetophenicol; Chloramphenicol; Chloramphenicol Palmitate; Chloramphenicol Pantothenate Complex; Chloramphenicol Sodium Succinate; Chlorhexidine Phosphanilate; Chloroxylenol; Chlortetracycline Bisulfate; Chlortetracycline Hydrochloride; Cinoxacin; Ciprofloxacin; Ciprofloxacin Hydrochloride; Cirolemycin; Clarithromycin; Clinafloxacin Hydrochloride; Clindamycin; Clindamycin Hydrochloride; Clindamycin Palmitate Hydrochloride; Clindamycin Phosphate; Clofazimine; Cloxacillin Benzathine; Cloxacillin Sodium; Cloxyquin; Colistimethate Sodium; Colistin Sulfate; Coumermycin; Coumermycin Sodium; Cyclacillin; Cycloserine; Dalfopristin; Dapsone; Daptomycin; Demeclocycline; Demeclocycline Hydrochloride; Demecycline; Denofungin; Diaveridine; Dicloxacillin; Dicloxacillin Sodium; Dihydrostreptomycin Sulfate; Dipyrithione; Dirithromycin; Doxycycline; Doxycycline Calcium; Doxycycline Fosfatex; Doxycycline Hyclate; Droxacin Sodium; Enoxacin; Epicillin; Epitetracycline Hydrochloride; Erythromycin; Erythromycin Acistrate; Erythromycin Estolate; Erythromycin Ethylsuccinate; Erythromycin Gluceptate; Erythromycin Lactobionate; Erythromycin Propionate; Erythromycin Stearate; Ethambutol Hydrochloride; Ethionamide; Fleroxacin; Floxacillin; Fludalanine; Flumequine; Fosfomycin; Fosfomycin Tromethamine; Fumoxicillin; Furazolium Chloride; Furazolium Tartrate; Fusidate Sodium; Fusidic Acid; Gentamicin Sulfate; Gloximonam; Gramicidin; Haloprogin; Hetacillin; Hetacillin Potassium; Hexedine; Ibafloxacin; Imipenem; Isoconazole; Isepamicin; Isoniazid; Josamycin; Kanamycin Sulfate; Kitasamycin; Levofuraltadone; Levopropylcillin Potassium; Lexithromycin; Lincomycin; Lincomycin Hydrochloride; Lomefloxacin; Lomefloxacin Hydrochloride; Lomefloxacin Mesylate; Loracarbef; Mafenide; Meclocycline; Meclocycline Sulfosalicylate; Megalomicin Potassium Phosphate; Mequidox; Meropenem; Methacycline; Methacycline Hydrochloride; Methenamine; Methenamine Hippurate; Methenamine Mandelate; Methicillin Sodium; Metioprim; Metronidazole Hydrochloride; Metronidazole Phosphate; Mezlocillin; Mezlocillin Sodium; Minocycline; Minocycline Hydrochloride; Mirincamycin lydrochloride; Monensin; Monensin Sodium; Nafcillin Sodium; Nalidixate Sodium; Nalidixic Acid; Natamycin; Nebramycin; Neomycin Palmitate; Neomycin Sulfate; Neomycin Undecylenate; Netilmicin Sulfate; Neutramycin; Nifuradene; Nifuraldezone; Nifuratel; Nifuratrone; Nifurdazil; Nifurimide; Nifurpirinol; Nifurquinazol; Nifurthiazole; Nitrocycline; Nitrofurantoin; Nitromide; Norfloxacin; Novobiocin Sodium; Ofloxacin; Ormetoprim; Oxacillin Sodium; Oximonam; Oximonam Sodium; Oxolinic Acid; Oxytetracycline; Oxytetracycline Calcium; Oxytetracycline Hydrochloride; Paldimycin; Parachlorophenol; Paulomycin; Pefloxacin; Pefloxacin Mesylate; Penamecillin; Penicillin G Benzathine; Penicillin G Potassium; Penicillin G Procaine; Penicillin G Sodium; Penicillin V; Penicillin V Benzathine; Penicillin V Hydrabamine; Penicillin V Potassium; Pentizidone Sodium; Phenyl Aminosalicylate; Piperacillin Sodium; Pirbenicillin Sodium; Piridicillin Sodium; Pirlimycin Hydrochloride; Pivampicillin Hydrochloride; Pivampicillin Pamoate; Pivampicillin Probenate; Polymyxin B Sulfate; Porfiromycin; Propikacin; Pyrazinamide; Pyrithione Zinc; Quindecamine Acetate; Quinupristin; Racephenicol; Ramoplanin; Ranimycin; Relomycin; Repromicin; Rifabutin; Rifametane; Rifamexil; Rifamide; Rifampin; Rifapentine; Rifaximin; Rolitetracycline; Rolitetracycline Nitrate; Rosaramicin; Rosaramicin Butyrate; Rosaramicin Propionate; Rosaramicin Sodium Phosphate; Rosaramicin Stearate; Rosoxacil; Roxarsone; Roxithromycin; Sancycline; Sanfetrinem Sodium; Sarmoxicillin; Sarpicillin; Scopafungin; Sisomicin; Sisomicin Sulfate; Sparfloxacin; Spectinomycin Hydrochloride; Spiramycin; Stallimycin Hydrochloride; Steffimycin; Streptomycin Sulfate; Streptonicozid; Sulfabenz: Sulfabenzamide; Sulfacetamide; Sulfacetamide Sodium; Sulfacytine; Sulfadiazine; Sulfadiazine Sodium; Sulfadoxine; Sulfalene; Sulfamerazine; Sulfameter: Sulfamethazine; Sulfamethizole; Sulfamethoxazole; Sulfamonomethoxine; Sulfamoxole; Sulfanilate Zinc; Sulfanitran; Sulfasalazine; Sulfasomizole; Sulfathiazole; Sulfazamet; Sulfisoxazole; Sulfisoxazole Acetyl; Sulfisoxazole Diolamine; Sulfomyxin; Sulopenem; Sultamicillin; Suncillin Sodium; Talampicillin Hydrochloride; Teicoplanin; Temafloxacin Hydrochloride; Temocillin; Tetracycline; Tetracycline Hydrochloride; Tetracycline Phosphate Complex; Tetroxoprim; Thiamphenicol; Thiphencillin Potassium; Ticarcillin Cresyl Sodium: Ticarcillin Disodium; Ticarcillin Monosodium; Ticlatone; Tiodonium Chloride; Tobramycin; Tobramycin Sulfate; Tosufloxacin; Trimethoprim; Trimethoprim Sulfate; Trisulfapyrimidines; Troleandomycin; Trospectomycin Sulfate; Tyrothricin; Vancomycin; Vancomycin Hydrochloride; Virginiamycin; Zorbamycin; Difloxacin Hydrochloride; Lauryl Isoquinolinium Bromide; Moxalactam Disodium; Ornidazole; Pentisomicin; and Sarafloxacin Hydrochloride.

Exemplary anti-cancer agents include Acivicin; Aclarubicin; Acodazole Hydrochloride; Acronine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexatc; Eflorithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-I a; Interferon Gamma-I b; Iproplatini; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Podofilox; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Sulofenur; Talisomycin; Taxotere; Tecogalan Sodium; Tegafur, Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporlin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate Virlrosidine Sulfate; Vinzolidine Sulfate; Vorozole; Zeniplatin; Zinostatin; and Zorubicin Hydrochloride.

Exemplary immunosuppressants include Azathioprine; Azathioprine Sodium; Cyclosporine; Daltroban; Gusperimus Trihydrochloride; Sirolimus; and Tacrolimus.

Exemplary anti-inflammatory agents include Alclofenac; Alclometasone Dipropionate; Algestone Acetonide; Alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lornoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Morniflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; and Zomepirac Sodium.

As used herein, "treatment" and/or "treating" refer to therapeutic treatment as well as prophylactic treatment or preventative measures. A compound selected from the group consisting of idebenone, benazepril, rolipram, moxonidine, lamivudine, loxoprofen, terbinafine, Synephrine, 6-aminoindazole, and a Vitamin D analog, or pharmaceutically acceptable salts thereof can be administered in pharmaceutical compositions comprising a pharmaceutically acceptable carrier or excipient. The excipient can be chosen based on the expected route of administration of the composition in therapeutic applications. The route of administration of the composition depends on the condition to be treated. For example, intravenous injection may be preferred for treatment of a systemic disorder and oral administration may be preferred to treat a gastrointestinal disorder. The route of administration and the dosage of the composition to be administered can be determined by the skilled artisan without undue experimentation in conjunction with standard dose-response studies. Relevant circumstances to be considered in making those determinations include the condition or conditions to be treated, the choice of composition to be administered, the age, weight, and response of the individual patient, and the severity of the patient's symptoms.

Pharmaceutical compositions comprising the compounds described above can be administered by a variety of routes including, but not limited to, parenteral, oral, pulmonary, ophthalmic, nasal, rectal, vaginal, aural, topical, buccal, transdermal, intravenous, intramuscular, subcutaneous, intradermal, intraocular, intracerebral, intralymphatic, intraarticular, intrathecal and intraperitoneal.

In one embodiment, the pharmaceutical composition can be administered orally. For the purpose of oral therapeutic administration, the pharmaceutical compositions can be incorporated with excipients and used in the form of tablets, troches, capsules, elixirs, suspensions, syrups, wafers, chewing gums and the like. Tablets, pills, capsules, troches and the like may also contain binders, excipients, disintegrating agent, lubricants, glidants, sweetening agents, and flavoring agents. Some examples of binders include microcrystalline cellulose, gum tragacanth or gelatin. Examples of excipients include starch or lactose. Some examples of disintegrating agents include alginic acid, corn starch and the like. Examples of lubricants include magnesium stearate or potassium stearate. An example of a glidant is colloidal silicon dioxide. Some examples of sweetening agents include sucrose, saccharin and the like. Examples of flavoring agents include peppermint, methyl salicylate, orange flavoring and the like. Materials used in preparing these various compositions should be pharmaceutically pure and non-toxic in the amounts used. In another embodiment, the composition is administered as a tablet or a capsule.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor, and the like. For vaginal administration, a pharmaceutical composition may be presented as pessaries, tampons, creams, gels, pastes, foams or spray.

The pharmaceutical composition can also be administered by nasal administration. As used herein, nasally administering or nasal administration includes administering the composition to the mucus membranes of the nasal passage or nasal cavity of the patient. As used herein, pharmaceutical compositions for nasal administration of a composition include therapeutically effective amounts of the compounds prepared by well-known methods to be administered, for example, as a nasal spray, nasal drop, suspension, gel, ointment, cream or powder. Administration of the composition may also take place using a nasal tampon or nasal sponge.

For topical administration, suitable formulations may include biocompatible oil, wax, gel, powder, polymer, or other liquid or solid carriers. Such formulations may be administered by applying directly to affected tissues, for example, a liquid formulation to treat infection of conjunctival tissue can be administered dropwise to the subject's eye, or a cream formulation can be administered to the skin.

The compositions can be administered parenterally such as, for example, by intravenous, intramuscular, intrathecal or subcutaneous injection. Parenteral administration can be accomplished by incorporating a composition into a solution or suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as, for example, benzyl alcohol or methyl parabens, antioxidants such as, for example, ascorbic acid or sodium bisulfite and chelating agents such as EDTA. Buffers such as acetates, citrates or phosphates and agents for the adjustment of tonicity such as sodium chloride or dextrose may also be added. The parenteral preparation can be enclosed in ampules, disposable syringes or multiple dose vials made of glass or plastic.

Rectal administration includes administering the pharmaceutical compositions into the rectum or large intestine. This can be accomplished using suppositories or enemas. Suppository formulations can easily be made by methods known in the art. For example, suppository formulations can be prepared by heating glycerin to about 120° C., dissolving the pharmaceutical composition in the glycerin, mixing the heated glycerin after which purified water may be added, and pouring the hot mixture into a suppository mold.

Transdermal administration includes percutaneous absorption of the composition through the skin. Transdermal formulations include patches, ointments, creams, gels, salves and the like.

In addition to the usual meaning of administering the formulations described herein to any part, tissue or organ whose primary function is gas exchange with the external environment, for purposes of the present invention, "pulmonary" will also mean to include a tissue or cavity that is contingent to the respiratory tract, in particular, the sinuses. For pulmonary administration, an aerosol formulation containing the active agent, a manual pump spray, nebulizer or pressurized metered-dose inhaler as well as dry powder formulations are contemplated. Suitable formulations of this type can also include other agents, such as antistatic agents, to maintain the disclosed compounds as effective aerosols.

A drug delivery device for delivering aerosols comprises a suitable aerosol canister with a metering valve containing a pharmaceutical aerosol formulation as described and an actuator housing adapted to hold the canister and allow for drug delivery. The canister in the drug delivery device has a head space representing greater than about 15% of the total volume of the canister. Often, the compound intended for pulmonary administration is dissolved, suspended or emulsified in a mixture of a solvent, surfactant and propellant. The mixture is maintained under pressure in a canister that has been sealed with a metering valve.

The invention is illustrated by the following examples which are not meant to be limiting in any way.

EXEMPLIFICATION

Example 1

Method of Determining Chemorepulsive and Chemoattractive Activity

The chemorepulsive activity of idebenone, benazepril, rolipram, moxonidine, lamivudine, calcitriol, calcipotriol, loxoprofen, terbinafine, Synephrine and 6-aminoindazole was determined as follows:
1. Prior to beginning the assay, the following were prepared:
   a. 0.5% Fetal Calf Serum (FCS) in Iscove's Modified Dulbecco's Medium (IMDM) (Assay Medium) (Both from ATCC).
   b. Migratory cells at a concentration of $2\times10^7$ cells/ml in Assay Medium.
   c. The indicated dilutions of the ligand of interest in Assay Medium were prepared.
2. The assay plates are Neuroprobe ChemoTx plates, part number 206-3 (3 um pore size) for neutrophils.
3. The plates were removed from packaging, leaving the membrane behind.
4. 31 µl of the following solutions were pipetted into each well:
   a. For media controls and for chemorepulsion samples, Assay Medium was used.
   b. For chemoattraction samples, appropriate dilution of ligand was used.
5. A sterile needle was used to pop any and all small bubbles present in each well.
6. The membrane was carefully placed onto the plate, starting at one side and then slowly lowering the other edge onto the plate.
7. 29 µl of the following were pipetted onto the top of each circle:
   a. For media controls and chemoattraction (CA) samples, use Assay Medium.
   b. For chemorepulsion (CR) samples, use the appropriate dilution of ligand.
8. 2 µl of cells (40,000 cells) were added to each bubble of liquid from step 7.
9. A needle was used to pop all air bubbles.
10. The plate was covered with the supplied lid and incubated for the desired time at 37° C. in 5% $CO_2$. Unless otherwise indicated, the incubation time was 1 hour for neutrophils and 3 hours for T cells. For monocytes and B cells, the incubation time was 2 hours.
11. After the desired assay time, the liquid was removed from the top of the plate using a Kimwipe. At this point, the plate was stored (with the membrane in place) for up to 2 hours at 4° C.
12. The membrane was carefully removed from the top of the plate and discard. The plate was examined under a microscope to look for ligand crystallization, contamination and overall migration.
13. White read plates were preloaded with 25 ul PBS.
14. Using a multichannel pipettor, 5 ul of Cell Titer Glo (Promega # G7572) was added to each well.
15. Using a multichannel pipettor set at 30 ul, lysed cell solution was transferred to white read plates pre-loaded with PBS.
16. The plate was read using the BioTek Synergy4 plate reader in order to quantify the number of migrated cells.

Idebenone, benazepril, rolipram, moxonidine, lamivudine, calcitriol, loxoprofen, terbinafine, synephrine and 6-aminoindazole showed chemorepulsion in at least two replicates that was greater than 2-fold over media.

Figure 1B:
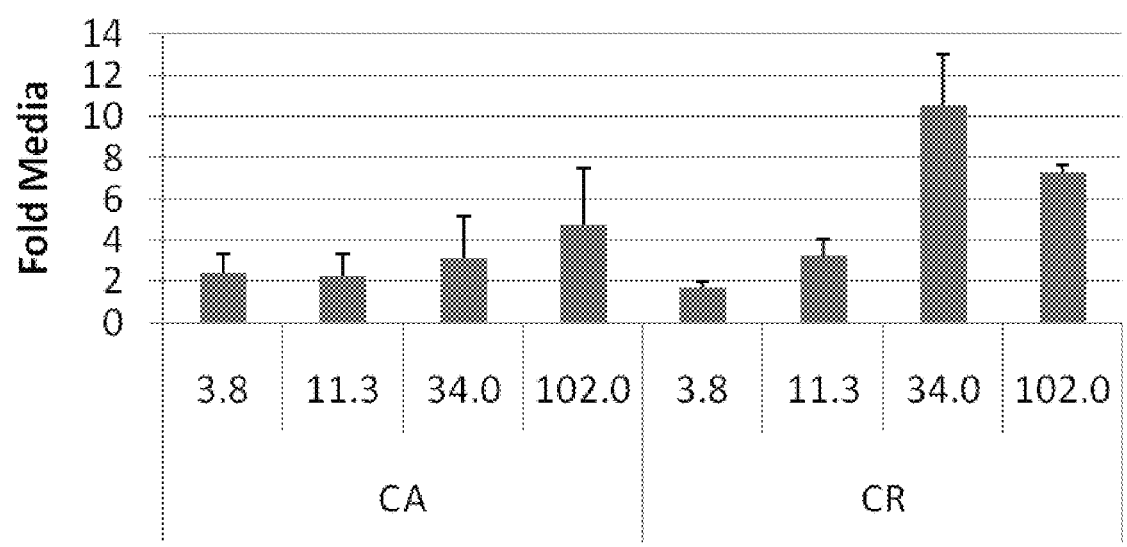
FIGS. 1B and 1C are bar graphs showing fold induction (over media) of chemorepulsion (right) and chemoattraction (left) of neutrophils treated with 3.8, 11.3, 34 and 102 uM idebenone.
Figure 1C:
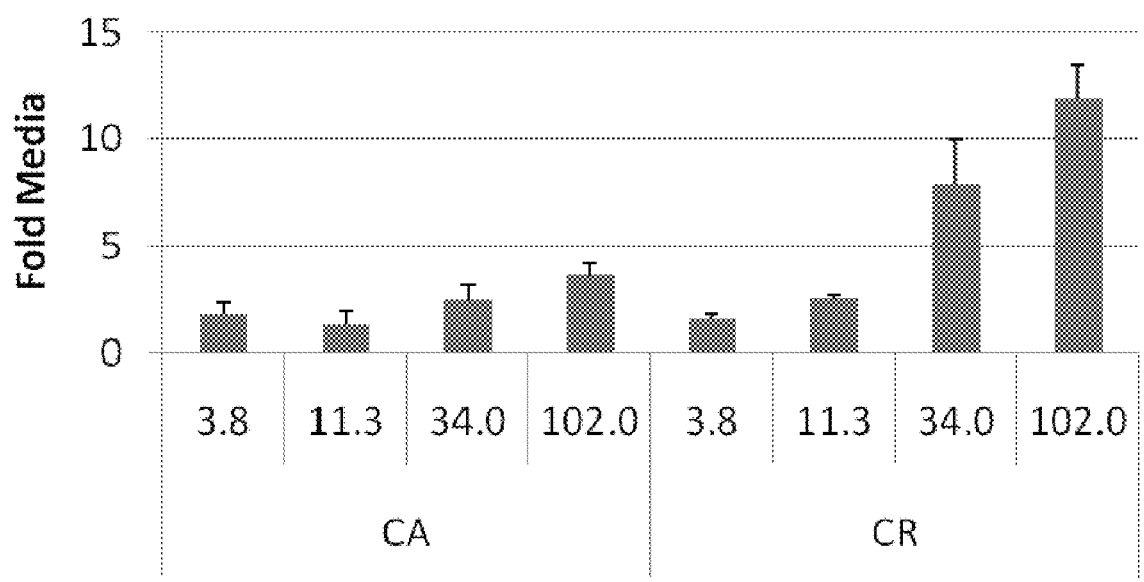

FIGS. 1A-C shows that neutrophils treated with 102 uM idebenone showed greater than 7-fold induction of chemorepulsion as compared to neutrophils treated with media.

Figure 2A:
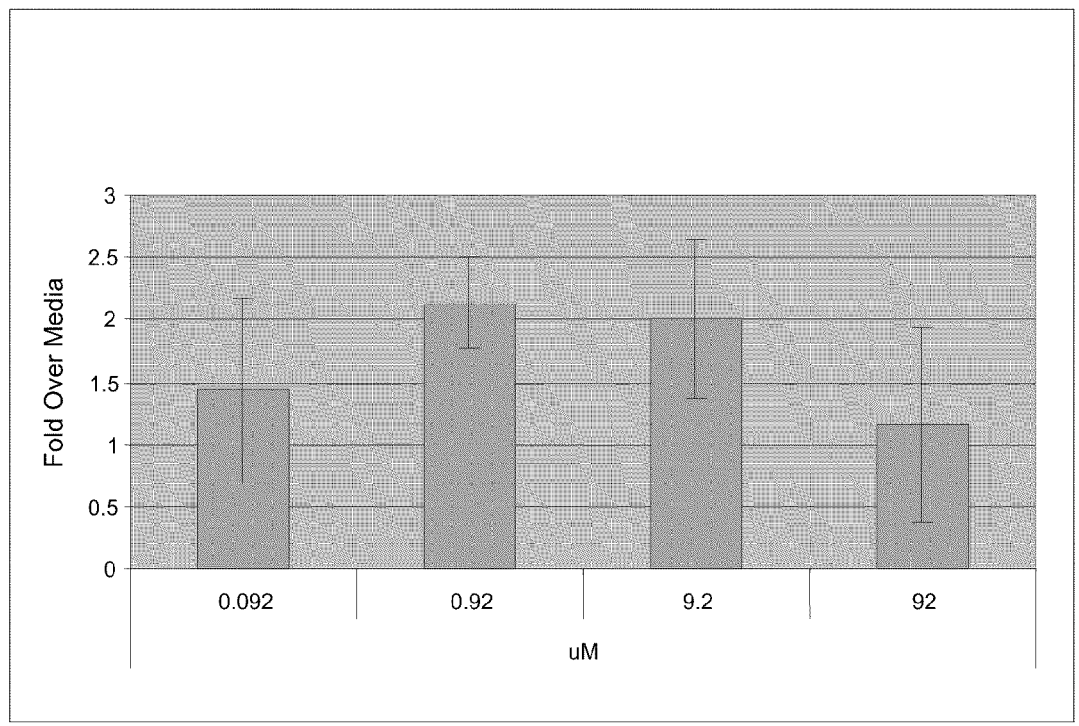
FIGS. 2A-C are bar graphs showing fold induction (over media) of chemorepulsion of neutrophils treated with 0.092, 0.92, 9.2 and 92 uM benazepril hydrochloride.
Figure 2B:
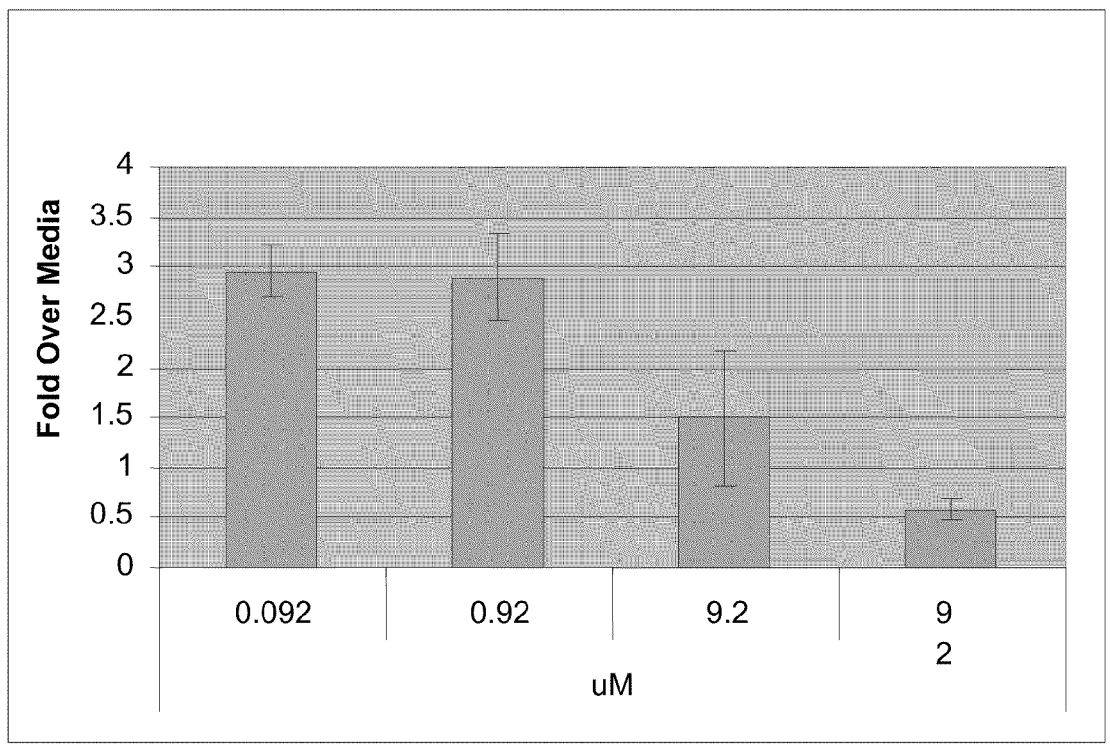
Figure 2C:
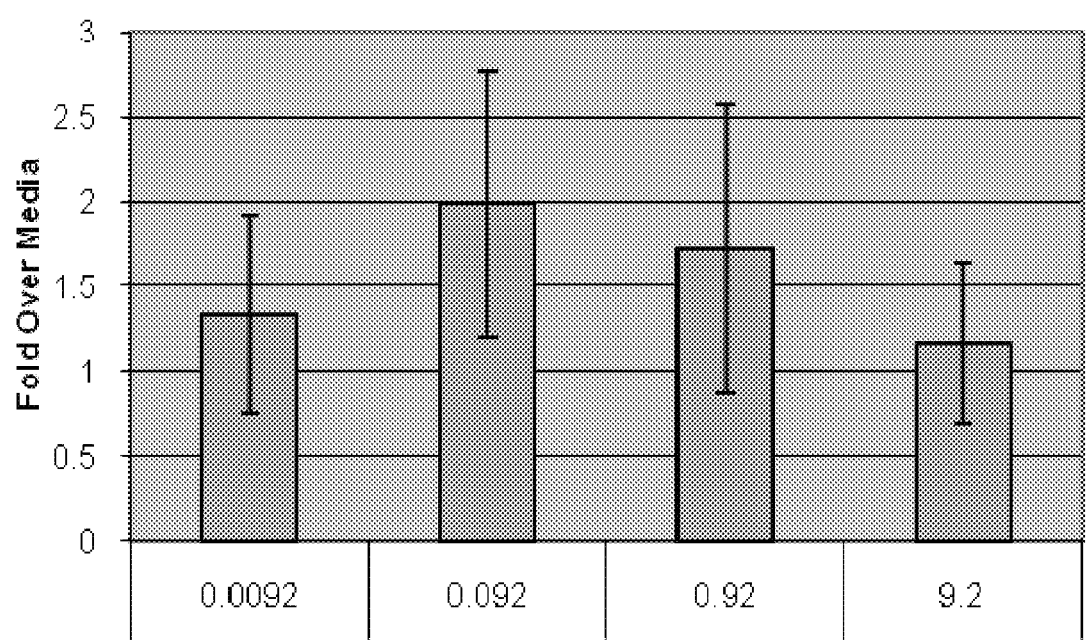

FIGS. 2A, B and C shows replicates in which neutrophils treated with 0.92 uM benazepril showed about 2-fold greater induction of chemorepulsion over media.

Figure 3A:
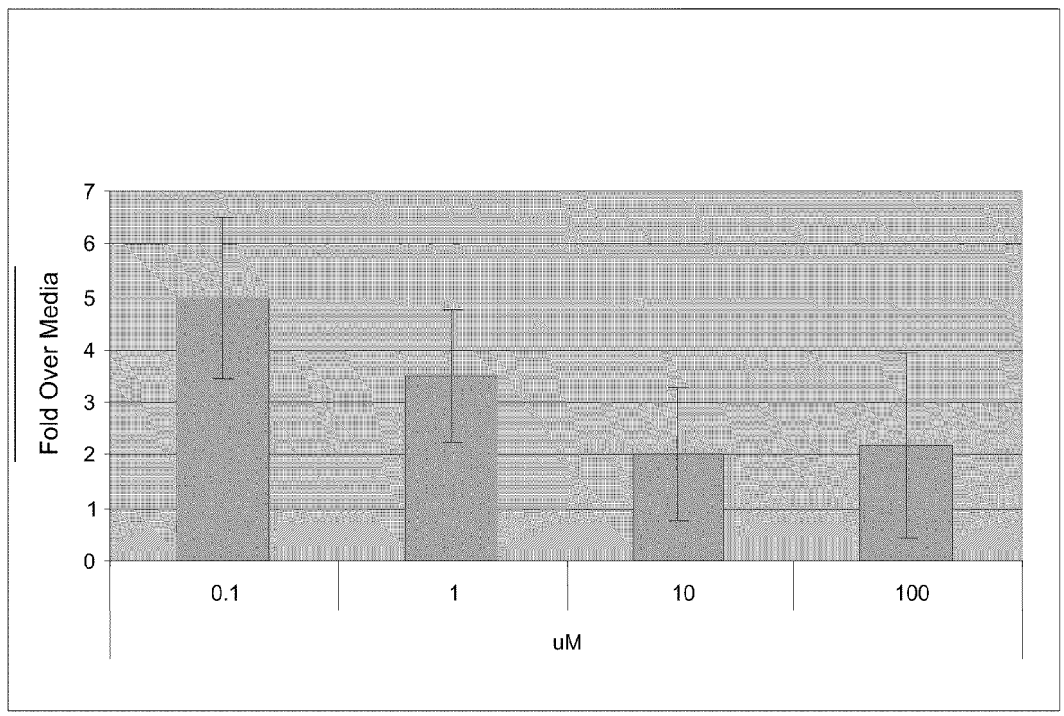
FIG. 3A is a bar graph showing fold induction (over media) of chemorepulsion of neutrophils treated with 0.1, 1, 10 and 100 uM rolipram.
Figure 3B:
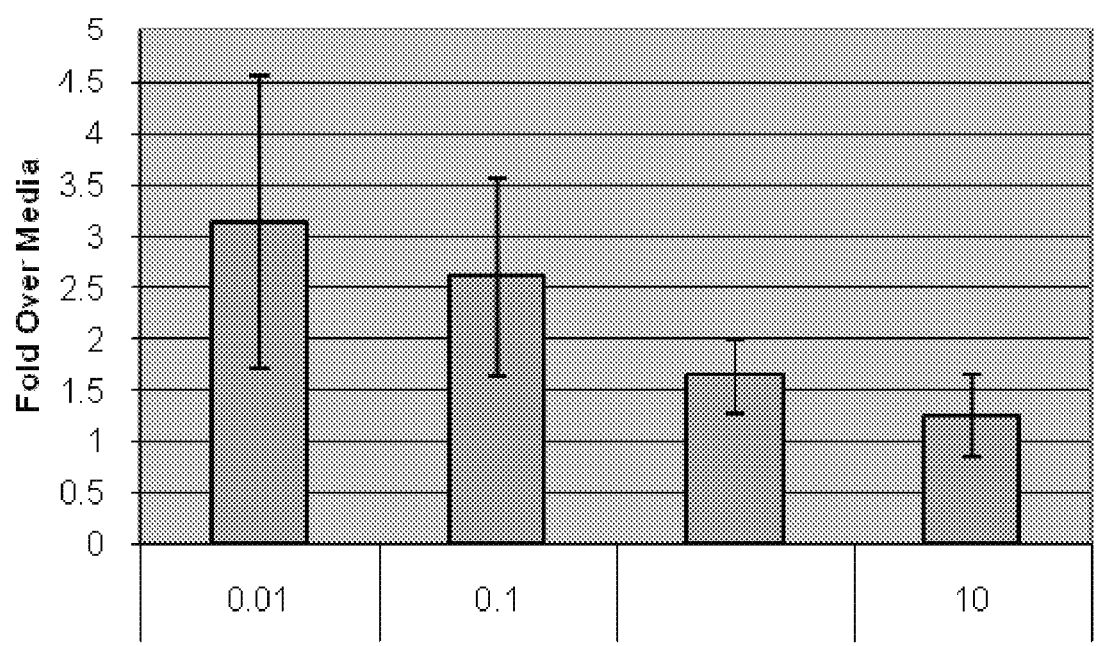
FIG. 3B is a bar graph showing fold induction (over media) of chemorepulsion of neutrophils treated with 0.01, 0.1, 1 and 10 uM rolipram.

FIGS. 3A and B shows replicates in which neutrophils treated with 0.1 uM rolipram showed 2-fold greater induction of chemorepulsion than those treated with media.

Figure 4A:
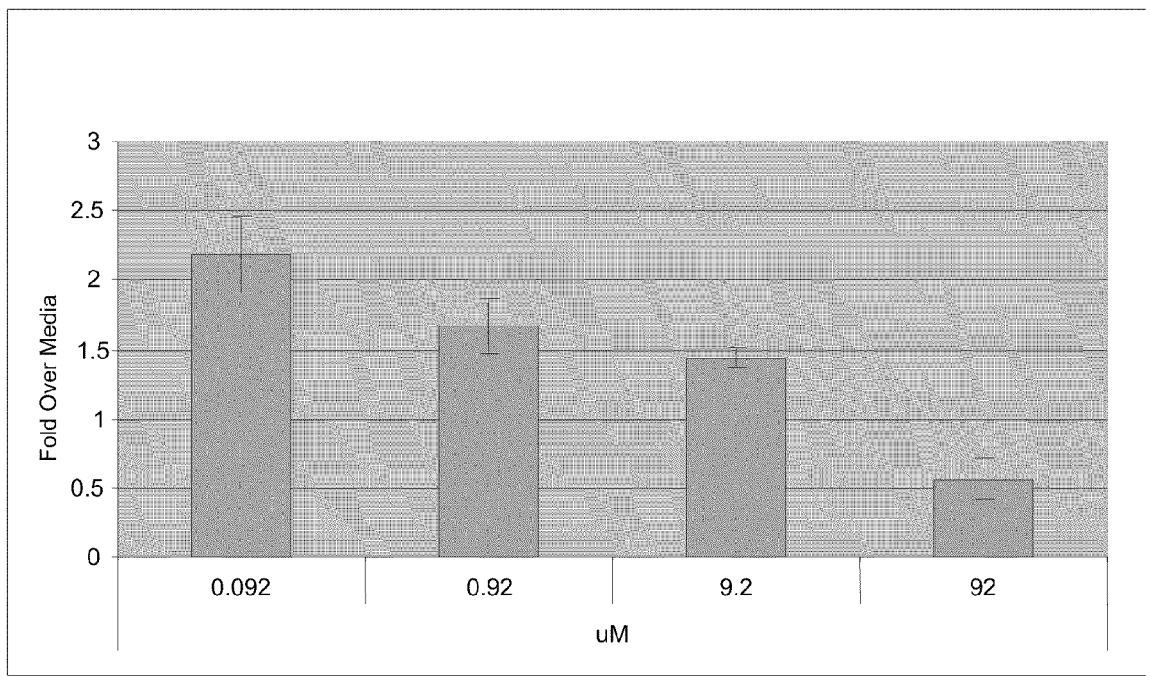
FIG. 4A is a bar graph showing fold induction (over media) of chemorepulsion of neutrophils treated with 0.092, 0.92, 9.2 and 92 uM moxonidine hydrochloride.
Figure 4B:
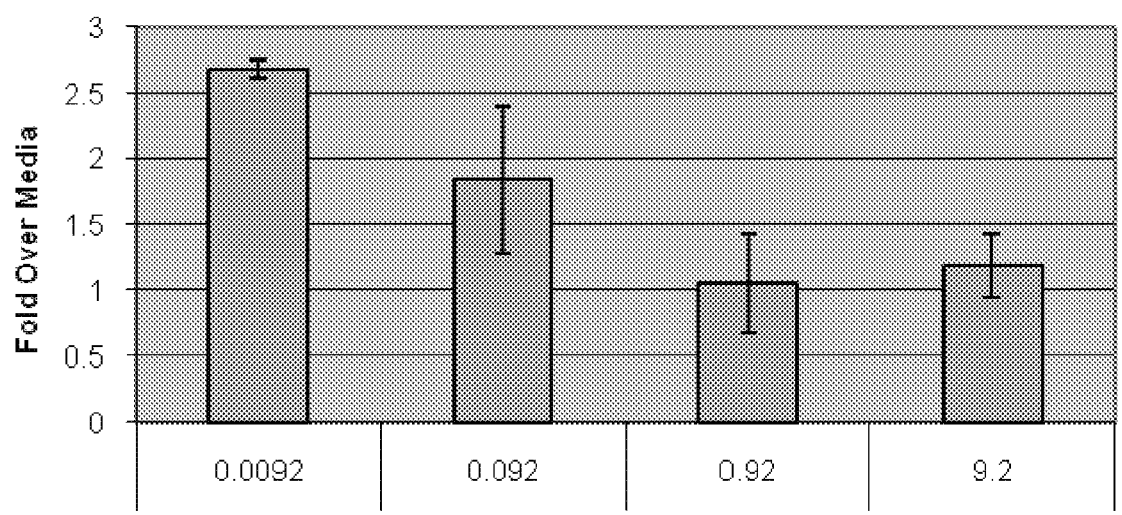
FIG. 4B is a bar graph showing fold induction (over media) of chemorepulsion of neutrophils treated with 0.0092, 0.092, 0.92 and 9.2 moxonidine hydrochloride.

FIGS. 4A and 4B shows replicates in which neutrophils treated with 0.092 uM moxonidine hydrochloride showed about 2-fold greater induction of chemorepulsion than neutrophils treated with media.

Figure 5A:
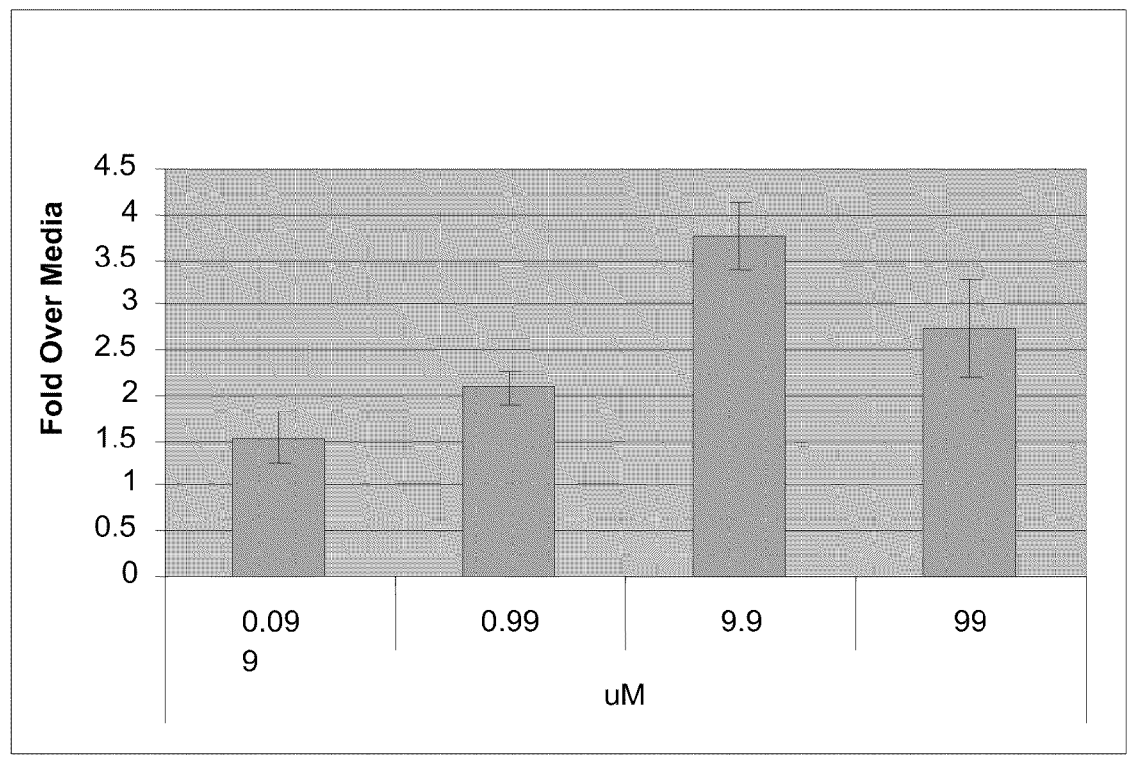
FIGS. 5A-B are bar graphs showing fold induction (over media) of chemorepulsion of neutrophils treated with 0.099, 0.99, 9.9 and 99 uM lamivudine.
Figure 5B:
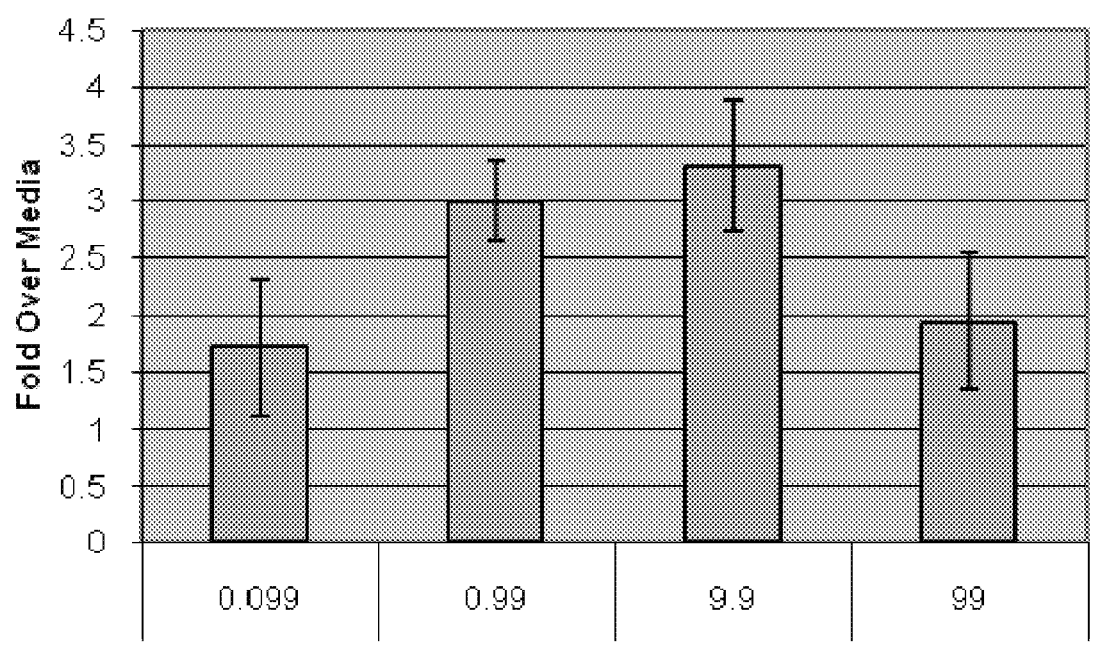

FIGS. 5A and 5B shows replicates in which neutrophils treated with 9.9 uM moxonidine showed greater than 2-fold induction of chemorepulsion than neutrophils treated with media.

Figure 6A:
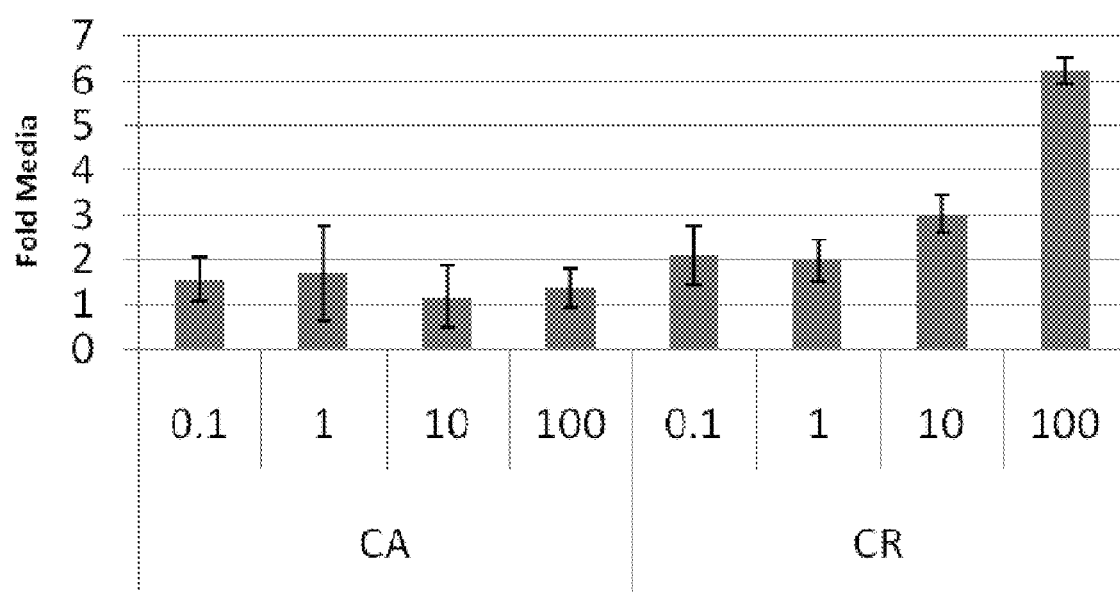
FIG. 6A is a bar graph showing fold induction (over media) of chemorepulsion (right) and chemoattraction (left) of neutrophils treated with 0.1, 1, 10 and 100 uM calcitriol.
Figure 6B:
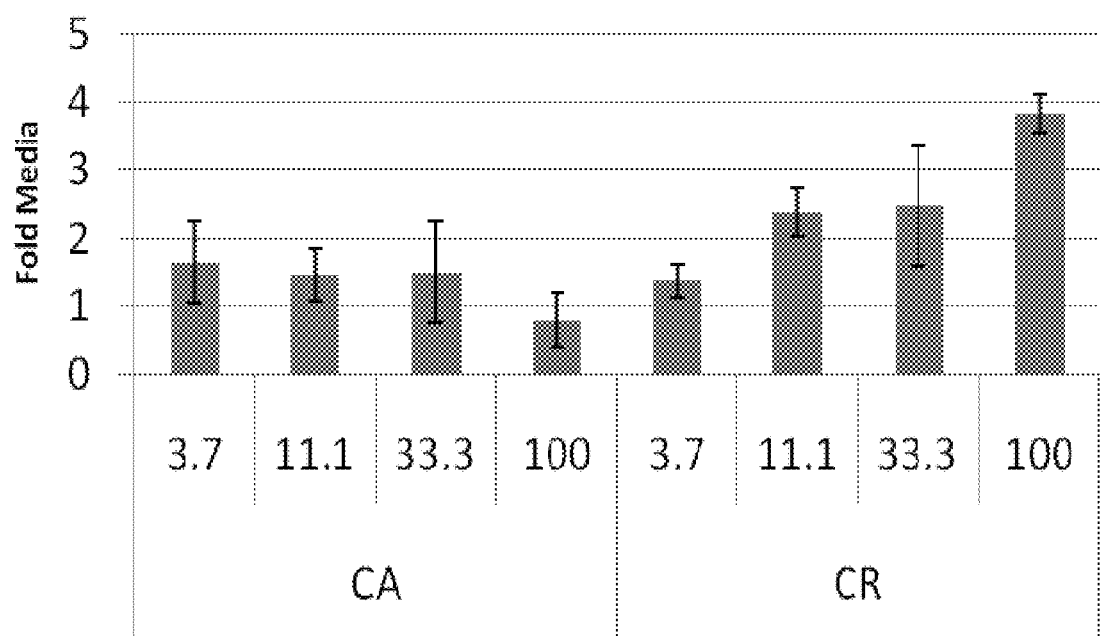
FIGS. 6B-C are bar graphs showing fold induction (over media) of chemorepulsion (right) and chemoattraction (left) of neutrophils treated with 3.7, 11.1, 33.3 and 100 uM calcitriol.
Figure 6C:
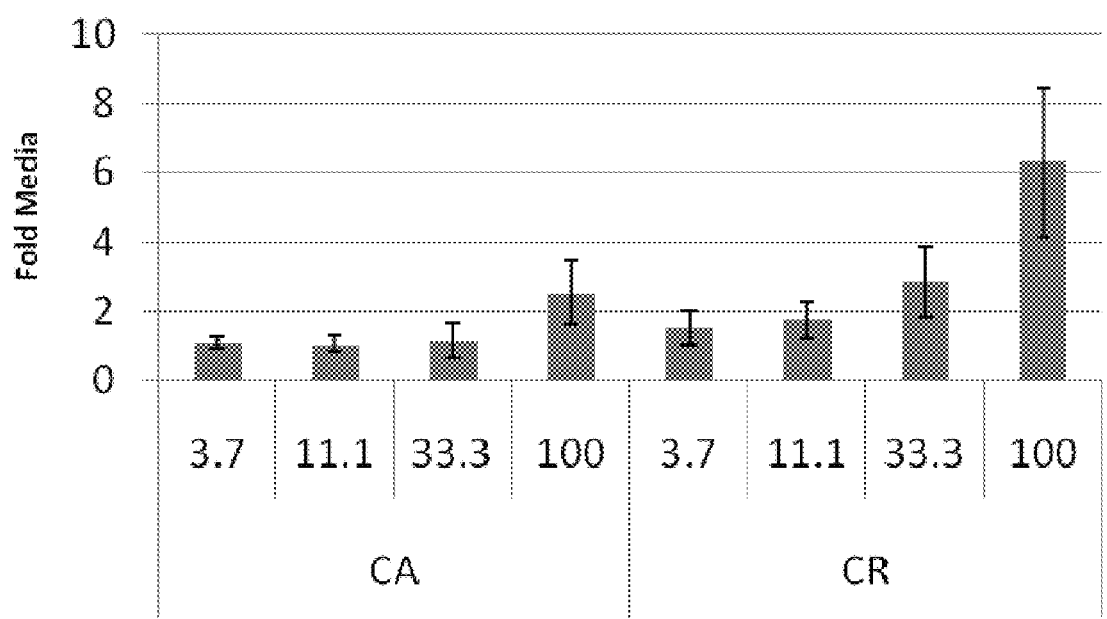

FIGS. 6A-C shows that neutrophils treated with 100 uM calcitriol showed greater than 3-fold induction of chemorepulsion than neutrophils treated with media.

Figure 7A:
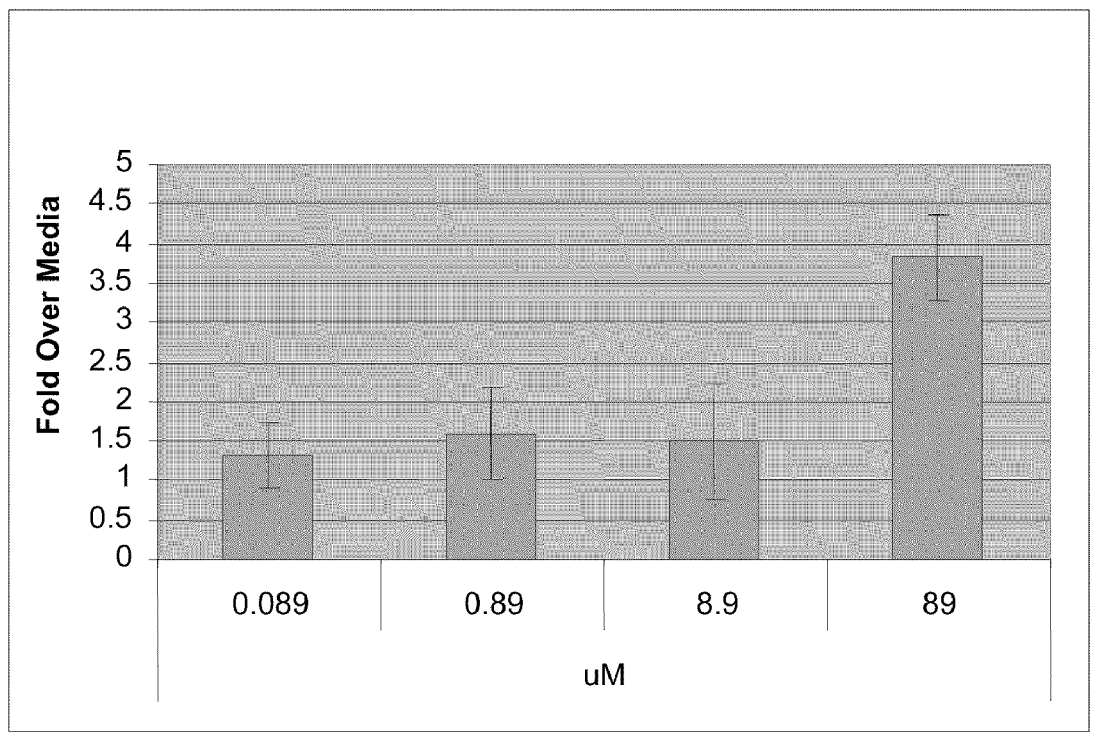
FIGS. 7A and B are bar graphs showing fold induction (over media) of chemorepulsion of neutrophils treated with 0.089, 0.89, 8.9 and 89 uM terbinafine hydrochloride.
Figure 7B:
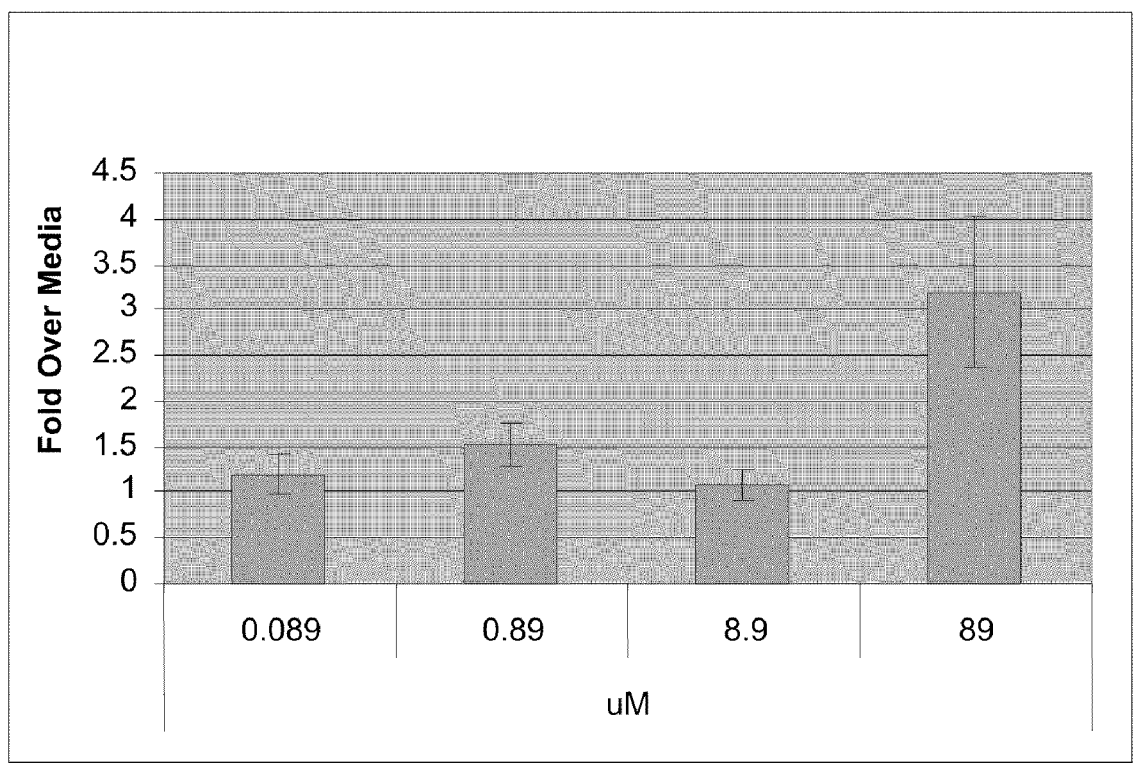
FIG. 7C is a bar graph showing fold induction (over media) of chemorepulsion (right) and chemoattraction (left) of neutrophils treated with 0.089, 0.89, 8.9 and 89 uM terbinafine hydrochloride.
Figure 7C:
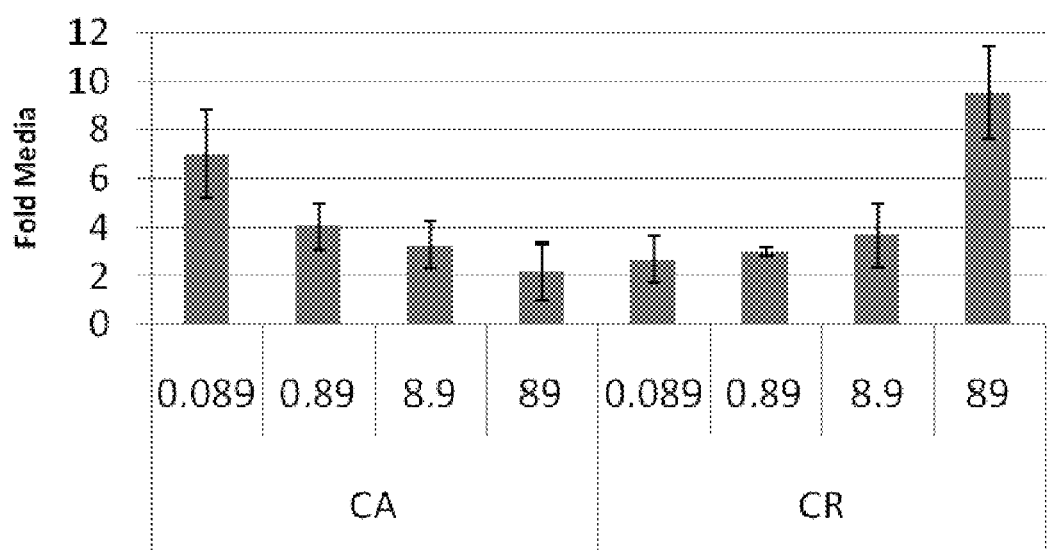

FIGS. 7A-C shows that neutrophils treated with 89 uM terbinafine hydrochloride showed greater than 2.5 fold induction of chemorepulsion than neutrophils treated with media.

Figure 8A:
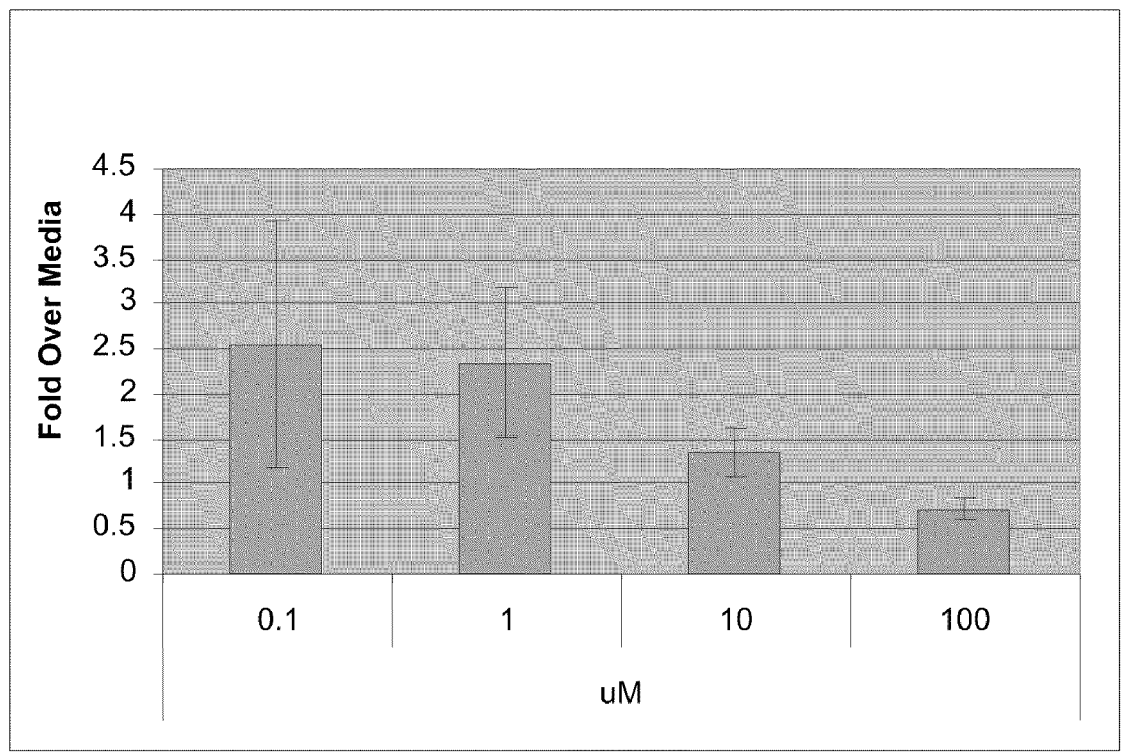
FIG. 8A is a bar graph showing fold induction (over media) of chemorepulsion of neutrophils treated with 0.1, 1, 10 and 100 uM synephrine.
Figure 8B:
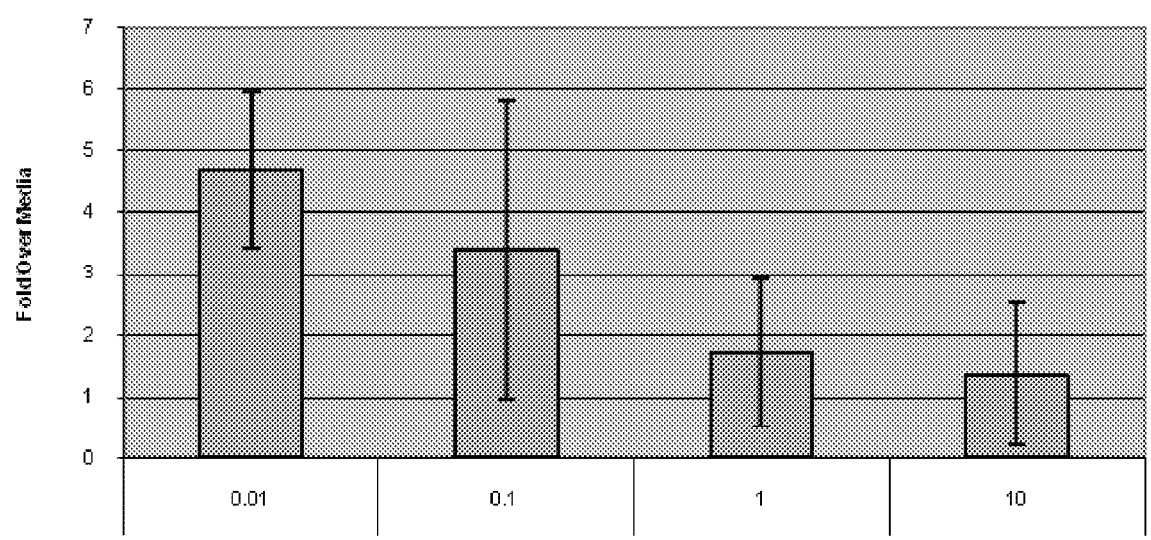
FIG. 8B is a bar graph showing fold induction (over media) of chemorepulsion of neuthrophils treated with 0.01, 0.1, 1 and 10 uM synephrine.

FIGS. 8A and B shows replicates in which neutrophils treated with 0.1 uM synephrine showed greater than 2-fold induction of chemorepulsion than neutrophils treated with media.

Figure 9A:
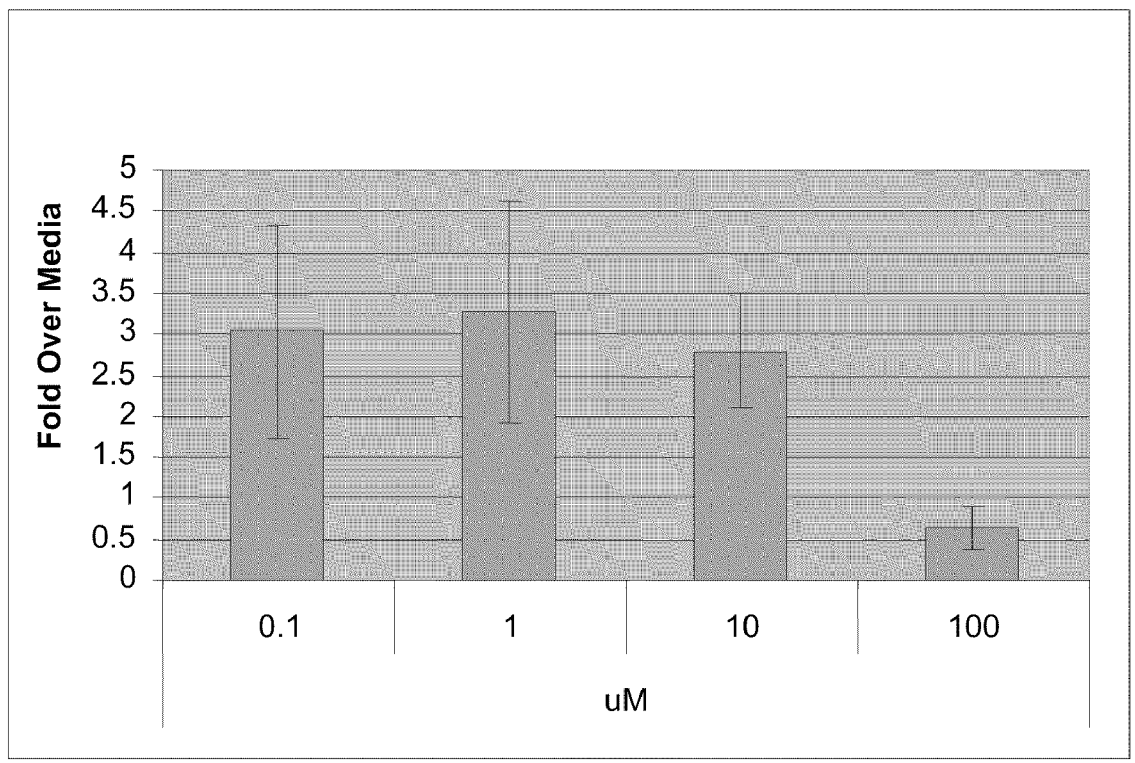
FIG. 9A is a bar graph showing fold induction (over media) of chemorepulsion of neutrophils treated with 0.1, 1, 10 and 100 uM 6-aminoindazole.
Figure 9B:
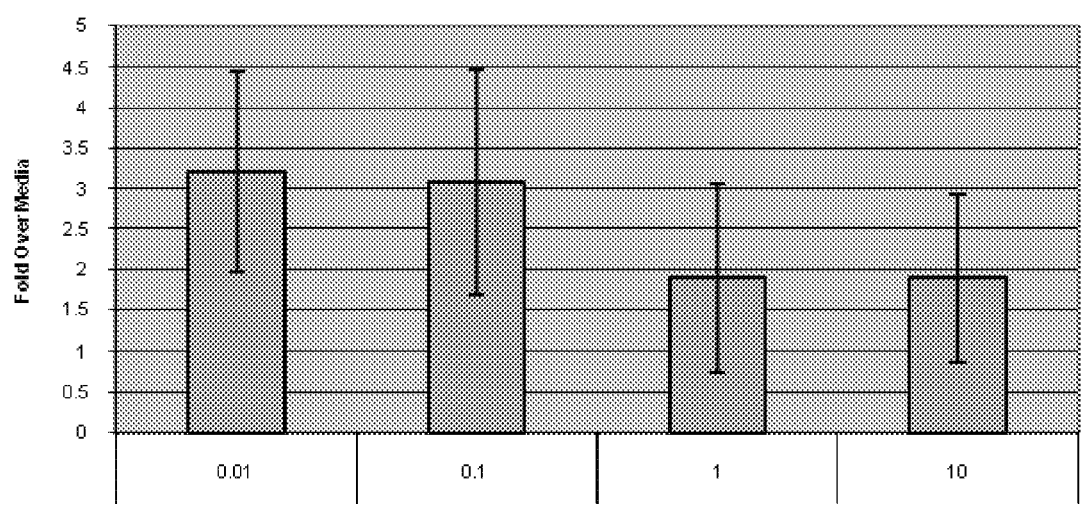
FIG. 9B is a bar graph showing fold induction (over media) of chemorepulsion of neutrophils treated with 0.01, 0.1, 1 and 10 uM 6-aminoindazole.

FIGS. 9A and B shows replicates in which neutrophils treated with 0.1 uM 6-aminoindazole showed greater than 3-fold induction of chemorepulsion than neutrophils treated with media.

Figure 10A:
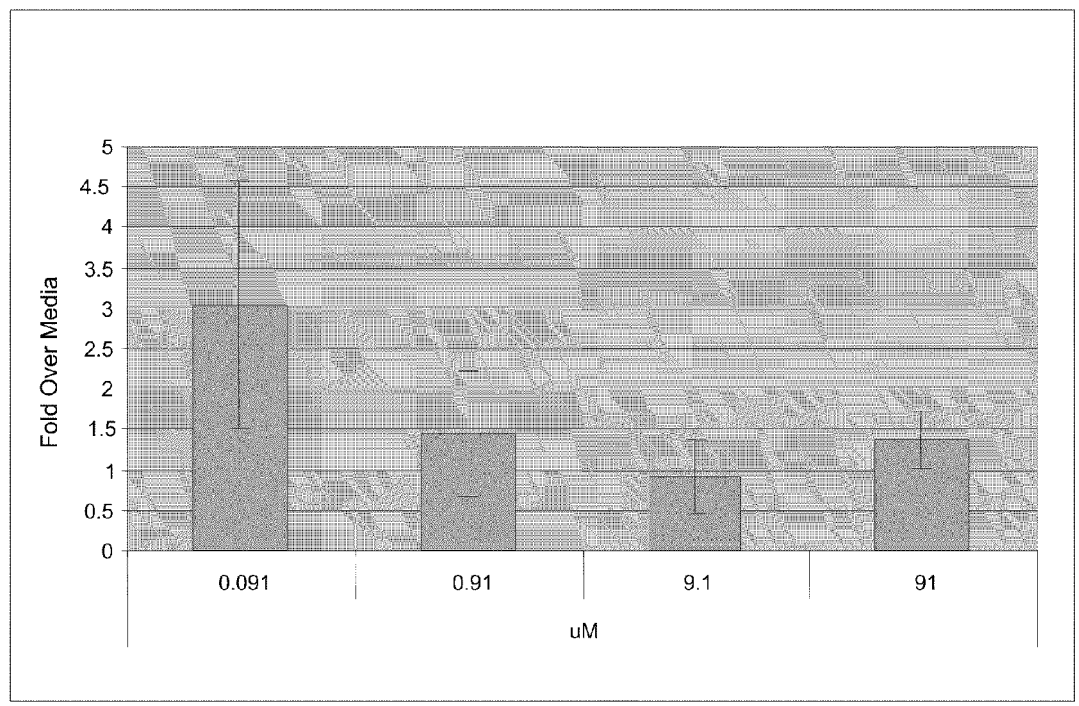
FIG. 10A is a bar graph showing fold induction (over media) of chemorepulsion of neutrophils treated with 0.091, 0.91, 9.1 and 91 uM loxoprofen sodium.
Figure 10B:
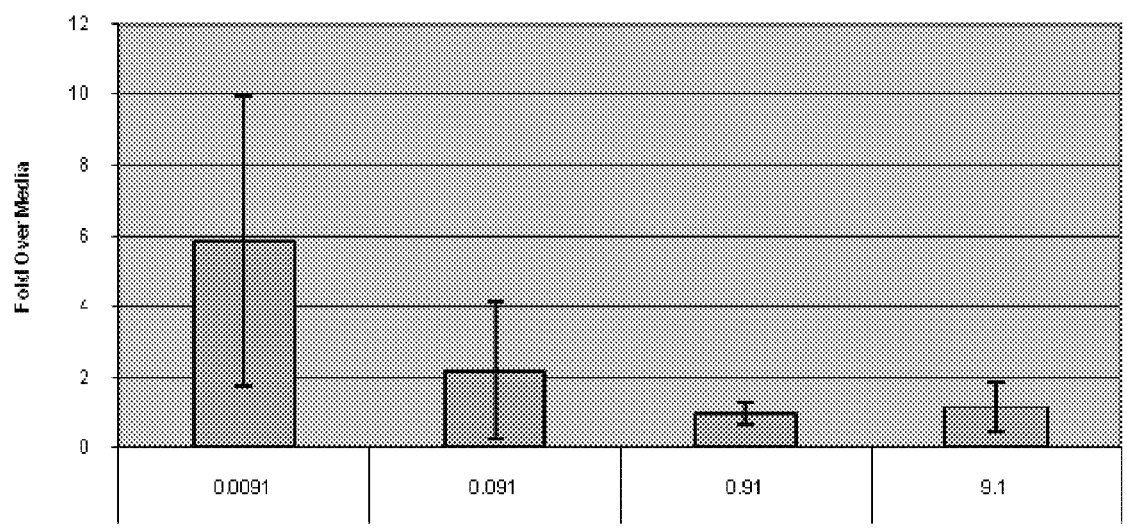
FIG. 10B is a bar graph showing fold induction (over media) of chemorepulsion of neutrophils treated with 0.0091, 0.091, 0.91 and 9.1 uM loxoprofen sodium.

FIGS. 10A and B shows replicates in which neutrophils treated with 0.091 uM loxoprofen sodium showed greater than 2-fold induction of chemorepulsion than neutrophils treated with media.

Example 2

Calcitriol Analogs

Figure 11:
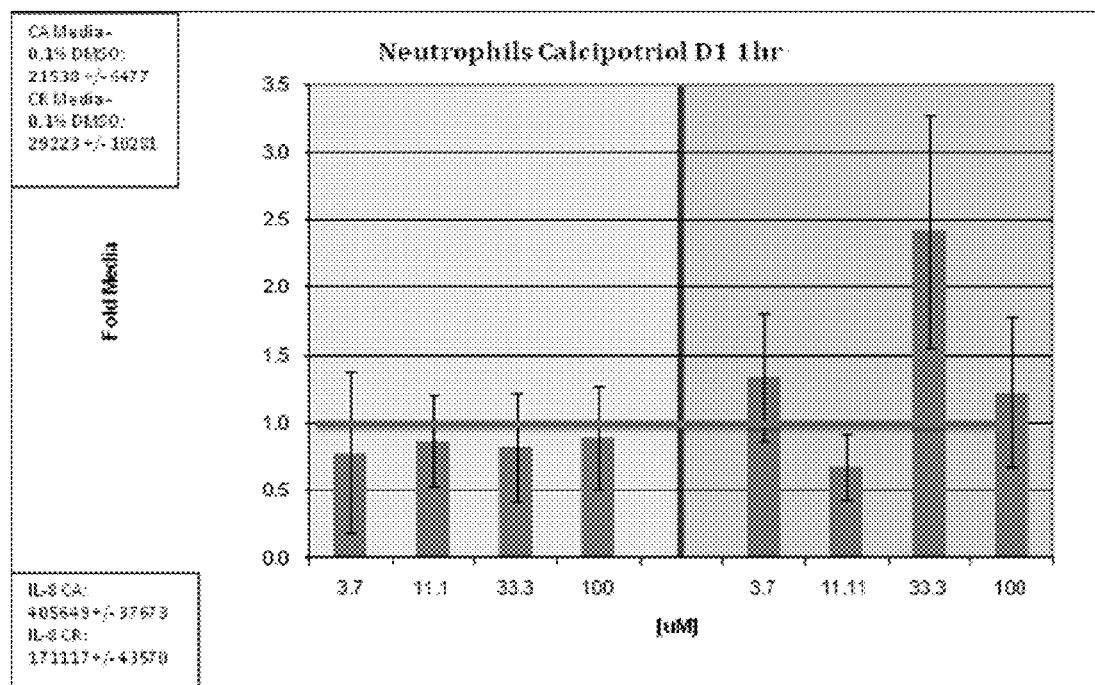
FIG. 11 is a plot of fold induction (over media) of chemorepulsion of neutrophils treated with 3.7, 11.1, 33.3 and 100 uM of calcipotriene.
Figure 12:
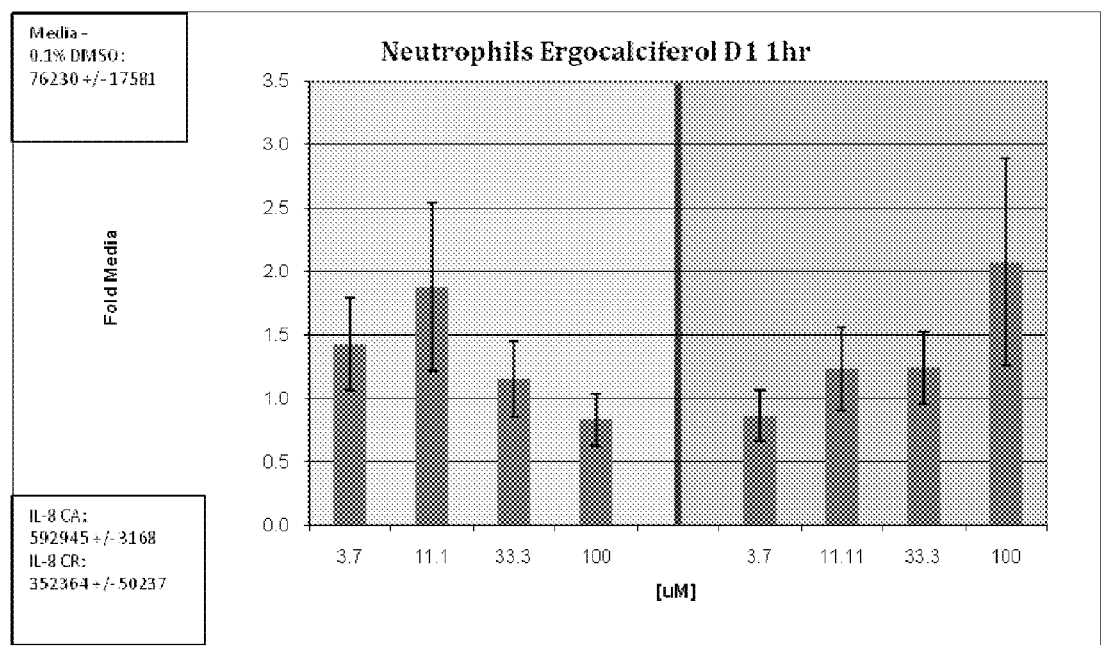
FIG. 12 is a plot of fold induction (over media) of chemorepulsion of neutrophils treated with 3.7, 11.1, 33.3 and 100 uM of Vitamin D2.
Figure 13:
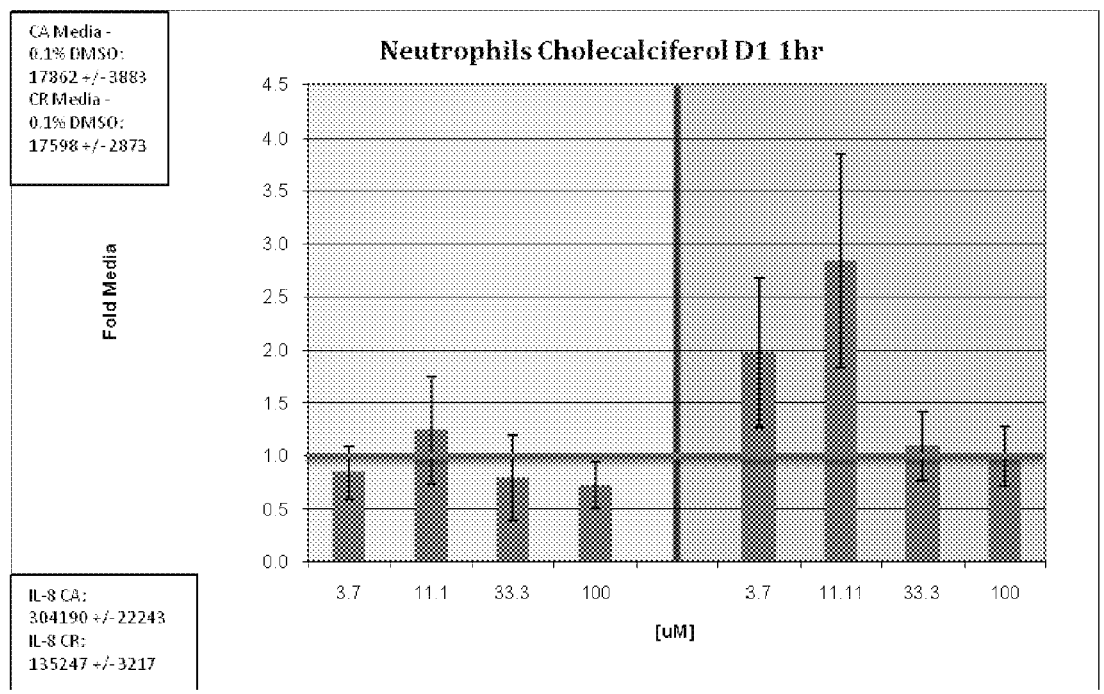
FIG. 13 is a plot of fold induction (over media) of chemorepulsion of neutrophils treated with 3.7, 11.1, 33.3 and 100 uM of Vitamin D3.
Figure 14:
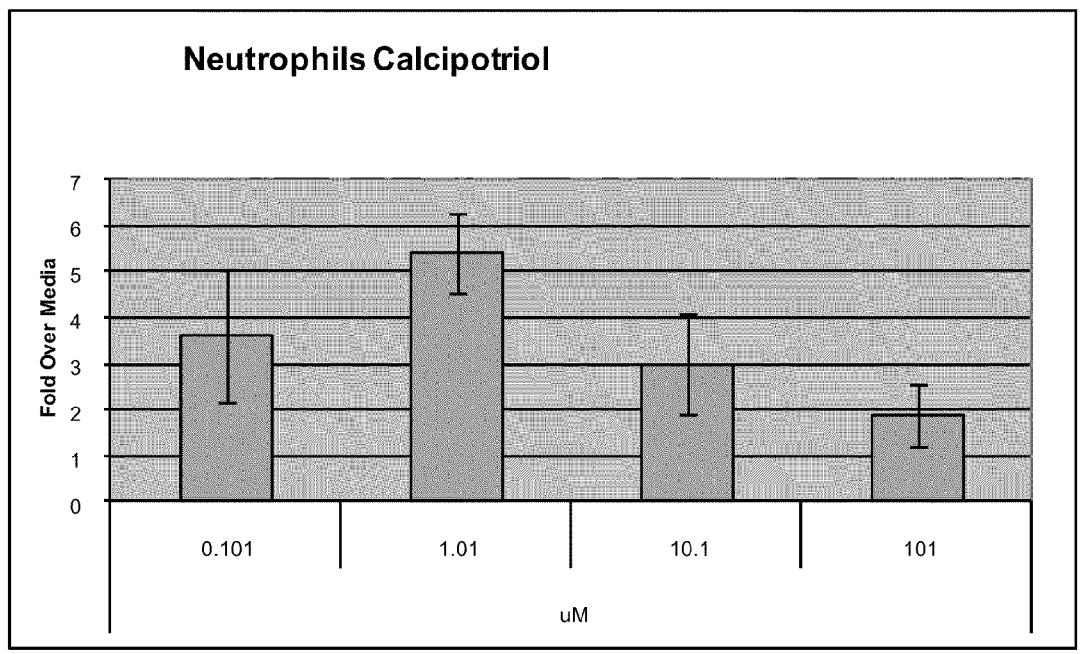
FIG. 14 is a bar graph showing fold induction (over media) of chemorepulsion of neutrophils treated with 0.101, 1.01, 10.1 and 101 uM calcipotriol.

The calcitriol analogs listed below were screened at concentrations of 3.7, 11.1, 33.3 and 100 uM as described above for chemorepulsive activity (FIGS. 11-13). FIG. 14 shows the chemorepulsive activity of calcipotriol at 0.101, 1.01, 10.1 and 100.1 uM, The activity of the Vitamin D analogs is shown below in Table 1.

TABLE 1

| Compound | Molecular Weight | Activity |
| --- | --- | --- |
| Calcipotriene | 412.6 | Chemorepellant |
| Vitamin D2 | 396.7 | Chemorepellant |
| Vitamin D3 | 384.6 | Chemorepellant |
| 1α-hydroxycholecalciferol (1α-OH-D3) | 400.6 | No activity |
| 1α-hydroxyvitamin D2 (1α OH-D2) | 412.7 | No activity |
| Calcefidiol | 400.6 | No activity |

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of inhibiting the chemotactic induction of an immune cell toward a site of inflammation in a patient suffering from an inflammatory condition comprising administering to said patient a therapeutically effective amount of terbinafine, or a pharmaceutically acceptable salt thereof, wherein the inflammatory condition is injection site reaction and wherein the site of inflammation is the site of the injection site reaction.

2. The method of claim 1 wherein terbinafine is administered locally to the site of inflammation.

3. The method of claim 1, wherein the immune cell is a neutrophil.

4. The method of claim 1, wherein the terbinafine is administered topically at the site of the injection.

* * * * *